US008558204B2

(12) United States Patent
Rees

(10) Patent No.: US 8,558,204 B2
(45) Date of Patent: Oct. 15, 2013

(54) SYSTEM AND METHOD FOR PROVIDING A SUSPENDED PERSONAL RADIATION PROTECTION SYSTEM

(75) Inventor: Chet R Rees, Dallas, TX (US)

(73) Assignee: Interventco, LLC, Dallas, TX (US)

( * ) Notice: Subject to any disclaimer, the term of this patent is extended or adjusted under 35 U.S.C. 154(b) by 608 days.

(21) Appl. No.: 12/692,199

(22) Filed: Jan. 22, 2010

(65) Prior Publication Data

US 2011/0174997 A1   Jul. 21, 2011

Related U.S. Application Data

(63) Continuation-in-part of application No. 12/688,353, filed on Jan. 15, 2010, which is a continuation-in-part of application No. 12/099,077, filed on Apr. 7, 2008, now Pat. No. 7,973,299.

(60) Provisional application No. 61/022,174, filed on Jan. 18, 2008.

(51) Int. Cl.
    G21F 3/02         (2006.01)
(52) U.S. Cl.
    CPC .................................. G21F 3/02 (2013.01)
    USPC ...................... 250/516.1; 250/519.1

(58) Field of Classification Search
    USPC .................. 250/516.1, 519.1, 515.1
    See application file for complete search history.

(56) References Cited

U.S. PATENT DOCUMENTS

| 4,254,341 | A | * | 3/1981 | Herr et al. ................. 250/519.1 |
| 4,581,538 | A | * | 4/1986 | Lenhart ..................... 250/519.1 |
| 4,843,641 | A | * | 7/1989 | Cusick et al. ..................... 2/457 |
| 5,015,864 | A | * | 5/1991 | Maleki ....................... 250/516.1 |
| 5,623,948 | A | * | 4/1997 | Van Morris ................. 5/81.1 R |
| 6,194,860 | B1 | * | 2/2001 | Seelinger et al. ............. 318/587 |
| 7,273,006 | B2 | * | 9/2007 | Rasmussen et al. ............ 101/32 |

* cited by examiner

Primary Examiner — Kiet T Nguyen
(74) Attorney, Agent, or Firm — Scott L. Harper; Harper Washam LLP

(57) ABSTRACT

An improved personal radiation protection system that substantially contours to an operator's body is suspended from a suspension means. The garment is operable to protect the operator from radiation. The suspension means is operable to provide constant force and allows the operator to move freely in the X, Y and Z planes simultaneously, such that the protective garment, face shield, or other attachments integrated into the system are substantially weightless to the operator. The suspension means may be mounted to the ceiling, a vertical wall, the floor, or on a mobile platform. The suspension means may comprise an articulating arm, a balance arm, or a manipulator, and the radiation protection system is suspended generally about its center of gravity.

11 Claims, 17 Drawing Sheets

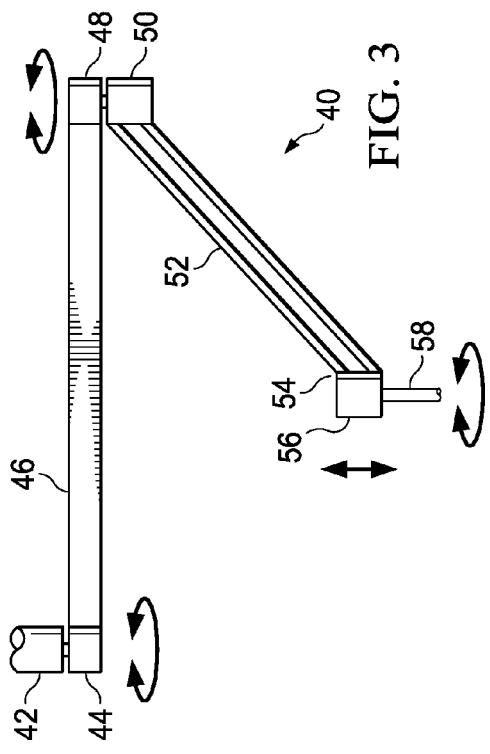
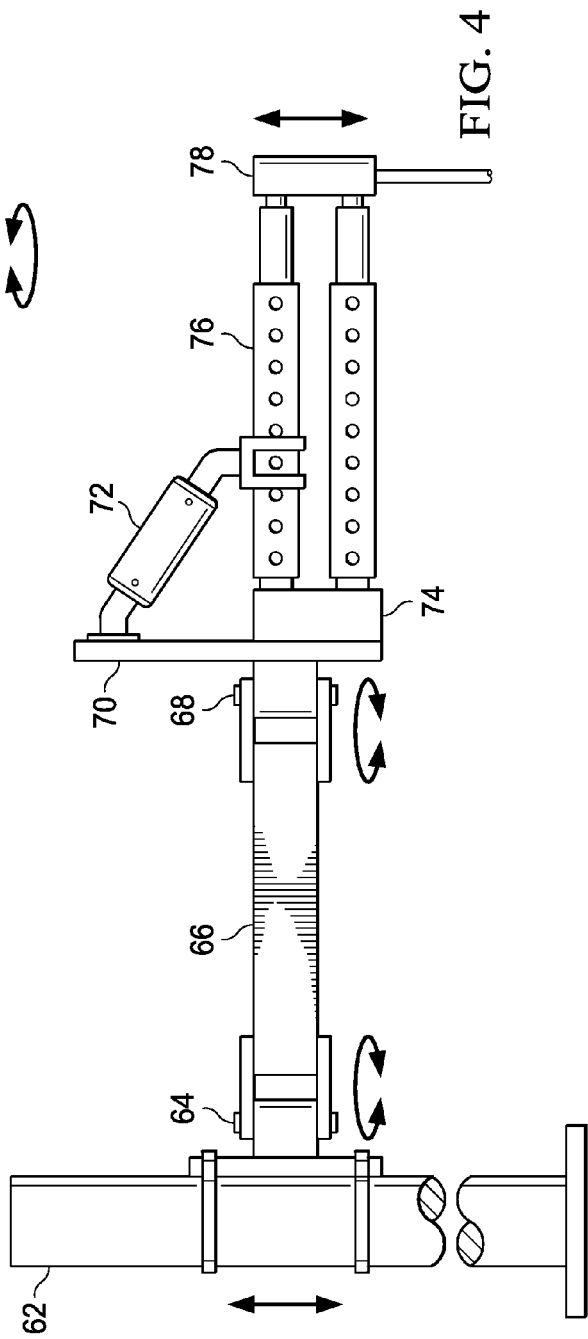

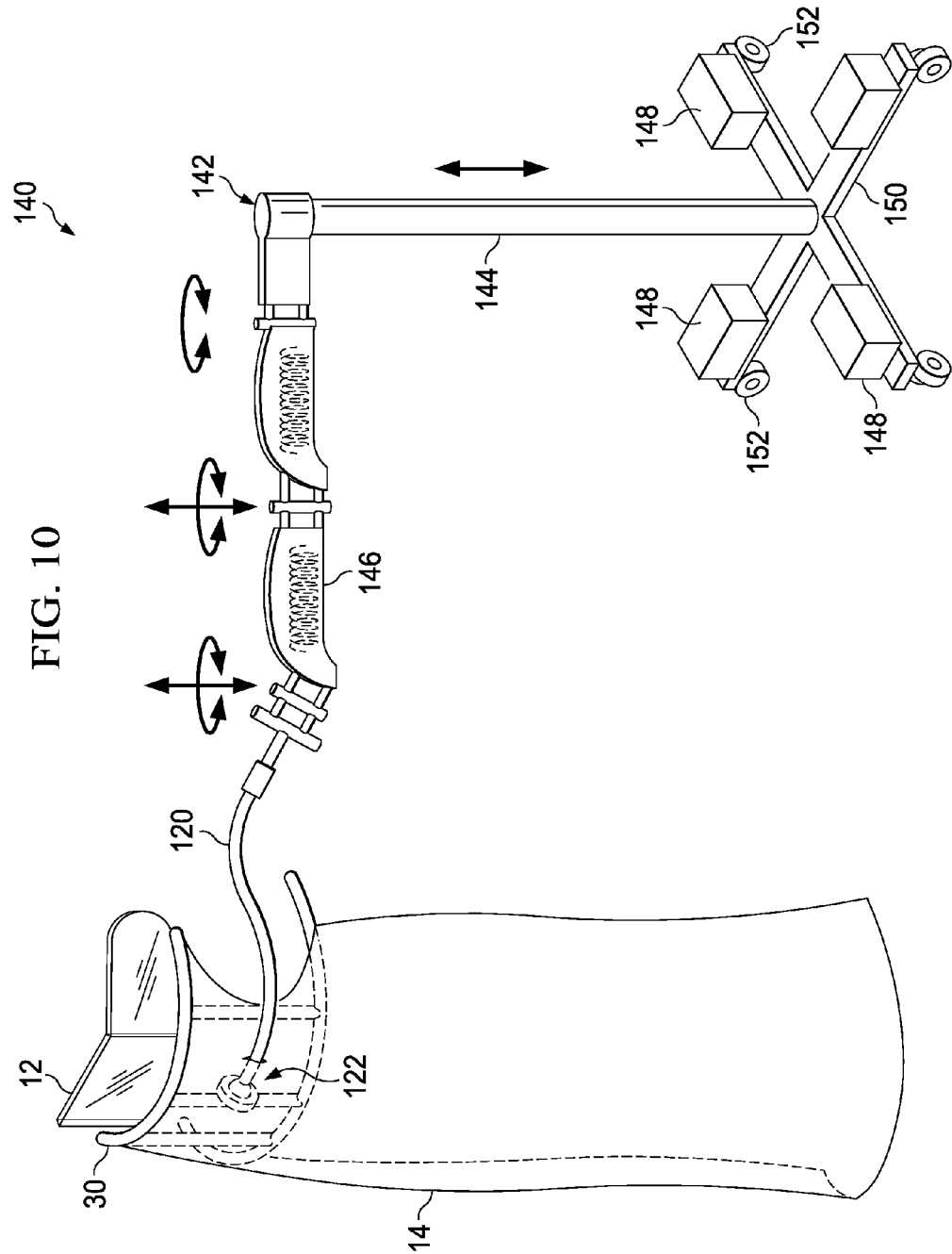

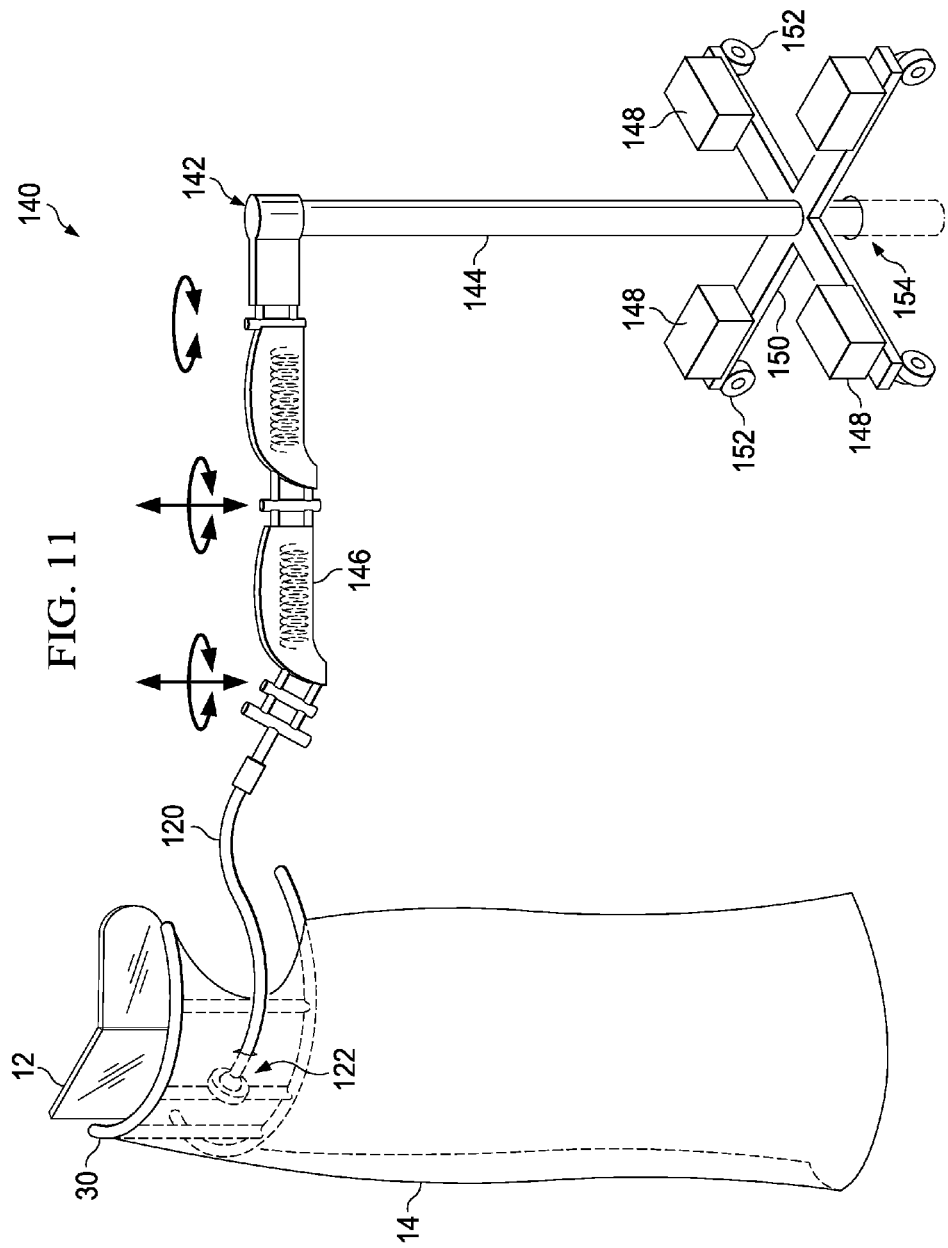

SYSTEM AND METHOD FOR PROVIDING A SUSPENDED PERSONAL RADIATION PROTECTION SYSTEM

CROSS-REFERENCE TO RELATED APPLICATIONS

This application is a continuation-in-part application and claims the benefit of and priority to co-pending U.S. patent application Ser. No. 12/688,353, filed on Jan. 15, 2010, which claims the benefit of and priority to U.S. patent application Ser. No. 12/099,077, filed on Apr. 7, 2008, now U.S. Pat. No. 7,973,299 which claims the benefit of and priority to U.S. provisional patent application Ser. No. 61/022,174, filed on Jan. 18, 2008. This application also claims the benefit of and priority to co-pending U.S. patent application Ser. No. 12/557,703, filed on Sep. 11, 2009, which claims the benefit of and priority to U.S. patent application Ser. No. 11/611,627, filed on Dec. 15, 2006 and which issued on Oct. 27, 2009 as U.S. Pat. No. 7,608,847, which claims the benefit of and priority to U.S. provisional patent application Ser. No. 60/751,371, filed on Dec. 16, 2005, the disclosures of which are hereby incorporated by reference.

TECHNICAL FIELD

The present invention relates in general to radiation protection and, more particularly, to a suspended personal radiation protection system.

BACKGROUND OF THE INVENTION

Radiation is used to perform many medical diagnostic and therapeutic tests and procedures. Medical, veterinary, or research personnel may be involved in the performance of these tests and procedures. These professionals are being exposed to scattered radiation as they perform their work. The long-term effects of this exposure are poorly understood at the present time, but are considered serious enough to warrant mandatory protection for operators, who are required to wear garments or barriers that contain materials, which absorb a significant proportion of the radiation. In order to properly perform tests or procedures on patients, operators require freedom of motion. Providing a personal radiation protection system and method that properly protects operators, while allowing operators to move freely and comfortably, presents a significant challenge for operators in radiation environments.

SUMMARY OF THE INVENTION

In accordance with the present invention, a method and apparatus for implementing a suspended personal radiation protection solution are provided as disclosed herein. According to one embodiment of the present invention, a system for offering radiation protection includes a garment that substantially contours to an operator's body. The garment protects the operator from a substantial portion of radiation which is scattered about during a treatment or testing procedure. The garment is supported by a suspension component that reduces a portion of the garment weight on the operator.

In one series of embodiments, jib cranes can be used for supporting the personal radiation protection system. Jib cranes typically utilize an arm that rotates around a post in the horizontal plane. A trolley can move along the arm of the jib, and anything may be suspended from the trolley, such as the radiation protection device and/or a balancing mechanism. When combined with a balancing mechanism to counteract the weight, it thus allows freedom of motion of the suspended object in the X, Y, Z spatial volume defined by the arc of the arm's rotation. The base may be attached to a ceiling, floor, wall, portable stand, or other fixed object. Many variations or enhancements upon the above described basic system can occur with jib systems.

In one series of embodiments of the radiation protection system, the suspension component comprises a reaction arm, manipulating arm, balancing arm, articulating arm, torque arm, and/or other rotating-jointed, articulating, mechanically assisted manipulator. In these embodiments, the garment is attached to a frame which is directly and rigidly secured to such articulating suspension component or components. This is in contrast to embodiments of related applications where the frame is suspended by rope or wire, which, in some circumstances, may undesirably introduce slack, suffer from delayed suspension component movements, or even cause backlash, which is a common problem encountered in any tethered arrangement.

Several terms exist for the above-mentioned rotating-jointed, articulating, mechanically assisted manipulators, such as: reaction arm, manipulating arm, torque arm, balancing arm, and articulating arm. Due to their similarity, they may be used herein interchangeably. In any case, there are at least two arms connected by joints that have at least one degree of freedom, and the joints are oriented such that the end load has at least two degrees of freedom. The end load can therefore move anywhere in the XY spatial planes by following any path. A third degree of freedom can be added for free motion in the XYZ volume either by adding joints in the system that allow vertical movement of the arms, combined with springs or pneumatic system for opposing gravity, or by using a vertical balancing system as described in related applications.

In accordance with a preferred embodiment of the present invention, the suspension apparatus connects to and supports the shield and/or garment device about its center of gravity or about a point or points in close proximity to the shield and/or garment's center of gravity. This improves motion with regard to certain operator movements, such as bending forward or sideways. Suspension of the shield and/or garment about its center of gravity, or substantially close to the center of gravity or in the coronal (frontal) plane containing the center of gravity, can be accomplished using a ball-in-socket joint along the garment frame, or by pivoting the garment frame about strategically placed axles or pivot joints.

In another embodiment of the present invention, a non-overhead means of suspension is discussed. The frame is supported at or near its center of gravity by a balancing arm, which is itself rotatably secured about the upright post of a floor-based stand. Floor-based docking and ceiling-based docking are possible as depicted herein. Variations of the floor-based stand may include: a mobile floor stand with wheels and counterbalancing weights; a mobile floor stand with an anchoring means for locking the floor stand in place; or, a mobile floor stand that is stabilized by a stationary ceiling post.

Another alternative embodiment of the present invention involves a portable, floor-based, shield and/or garment-suspending back table. Such a back table can comprise a portable track stand which allows lateral sliding movement of a balancing arm for suspending the radiation shield/garment. Alternatively, the shield/garment can be suspended by a table-mounted manipulator arm, articulating arm, reaction arm, or balancing arm which can be rotatably secured to the back table by a table-mounted upright post. Several means for securing the back table to the floor are disclosed, including: stowable floor hooks, floor rings, lockable table wheels, and/or counterbalancing weights or a combination thereof.

Other technical advantages of the present invention will be readily apparent to one skilled in the art from the following figures, descriptions and claims. While specific advantages and embodiments have been enumerated above, various embodiments may include all, some, or none of the enumerated advantages.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

FIG. 3 is an elevated side view of the manipulator-arm/reaction-arm-type suspension system in accordance with the present invention;

FIG. 4 is an elevated side view of an alternative suspension system in accordance with the present invention;

FIG. 10 is a perspective side view of a portable, floor-based, non-overhead suspension system in accordance with the present invention;

FIG. 11 is a perspective side view of the portable, floor-based, non-overhead suspension system of FIG. 10 modified for floor-based docking, in accordance with the present invention;

DETAILED DESCRIPTION OF THE INVENTION

Figure 1:
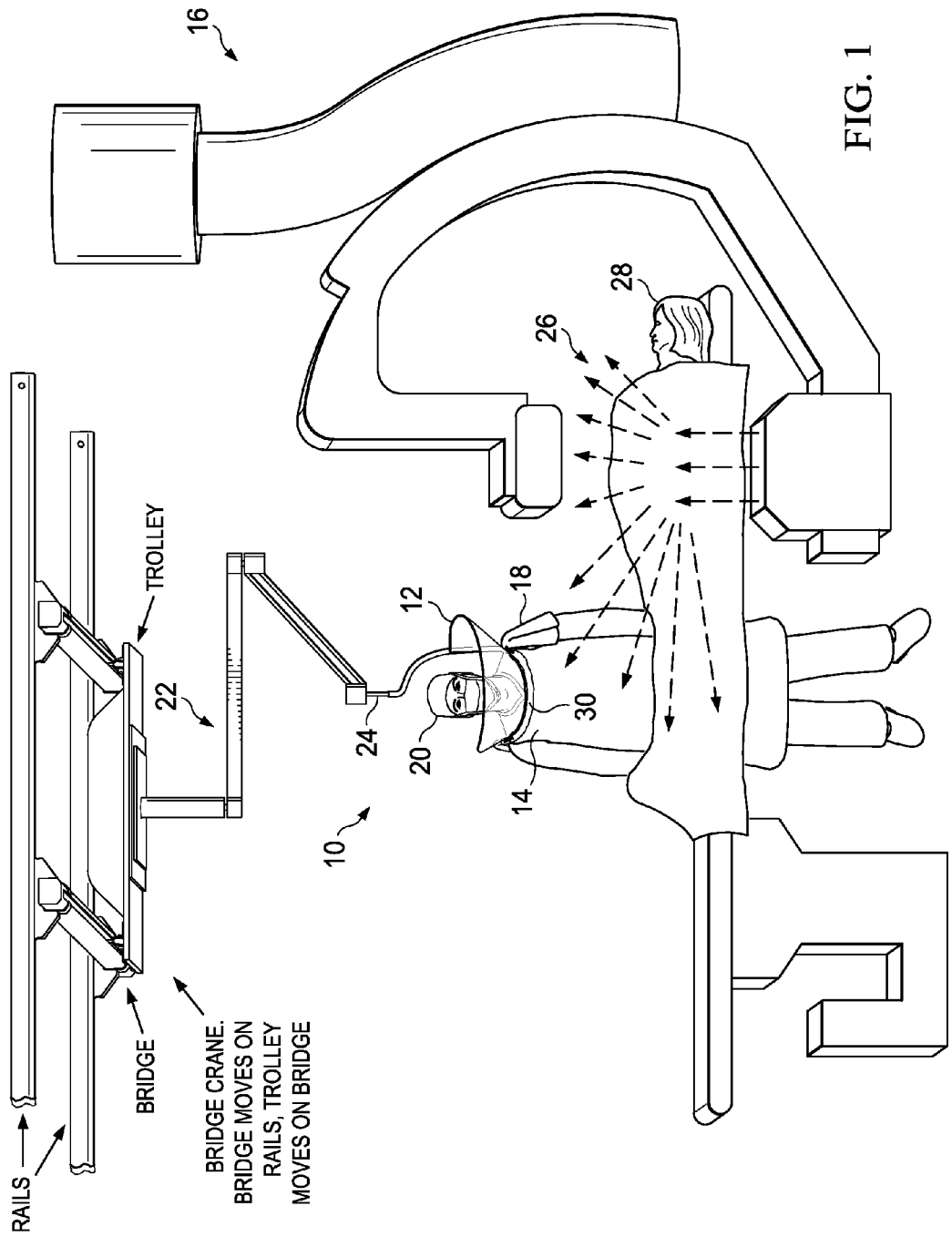
FIG. 1 is a perspective view of a suspended personal radiation protection system in accordance with the present invention.

For purposes of teaching and discussion, it is useful to provide some overview as to the way in which the invention disclosed herein operates. The following information may be viewed as a basis from which the present invention may by properly explained. Such information is offered for purposes of explanation only and, accordingly, should not be construed to limit the broad scope of the present invention and its potential applications.

Radiation is used to perform many medical diagnostic and therapeutic tests and procedures. The human patient or animal is subjected to radiation using minimal doses to enable completion of the medical task. Exposures to radiation are monitored to prevent or reduce risks of significant damage. Medical, veterinary, or research personnel may be involved in the performance of such procedures in great numbers.

Over many years, these professionals are being exposed to scattered radiation as they perform their work. Although their daily exposure is generally less than that for the patient, there are adverse cumulative effects to the operators. These long-term effects are poorly understood but are considered serious enough to warrant mandatory protection to workers in the form of garments or barriers that absorb a significant proportion of the radiation. There is a wide variety of such barriers commercially available, but these solutions have significant limitations for the operators who must come in close contact with the subject. These operators may be physicians and their assistants, or technically skilled medical personnel, who perform simple or complex medical procedures using their bodies and hands in proximity of the patient. In many cases, scatter radiation from the subject or physical elements in the direct radiation beam will pose significant health risks and unacceptably high exposure.

Risks of radiation exposure at the levels of medical personnel include cancers, cataracts, skin damage, etc. A review of current protective systems outlines their limitations. Radiation-absorbing walls are useful to contain the radiation to a room, but do not prevent exposures within their confines. Barriers within the room (such as floor or ceiling supported shields) are effective at blocking radiation for personnel who are not in close contact with the radiation field (such as some nurses and technologists) but must be positioned or repositioned frequently when personnel move around the room. They also provide cumbersome interference for operators performing the actual medical procedure. They may also be difficult to keep sterile when attempting to use them within the sterile field.

The most commonly used protection for operators involves the use of garments containing radiation-absorbing materials, generally lead or other metals, which are worn in the fashion of a coat, smock, skirt, vest, etc. and do not contaminate the sterile field because they are worn underneath the sterile covering gown. These garments are heavy and uncomfortable, and their long-term usage is known to be associated with diseases of the spine (in the neck and back), knee disorders, and other musculoskeletal problems, which can result in disability, medical expenses, and decreased quality of life for the operator.

The trade-off between protection and garment weight results in the frequent use of garments that do not cover the legs, head, torso, and eyes optimally, and may provide suboptimal radiation protection due to the thickness of the metallic material being limited by the tolerability of the operator. To protect other radiation-sensitive tissues (such as the corneas of the eye and the thyroid), special heavy glasses containing metallic compounds and a collar around the neck are often worn. Even when the operator is encumbered with these items, the base of the skull (which may contain sensitive bone marrow) and the face are still unprotected. Personal face and neck shields address this problem, and are commercially available, but are rarely worn due to their cumbersome nature and heavy weight.

Such problems have been present for many years and there are current solutions that attempt to address them. Modifications to floor-supported mobile shields appear to attempt to provide improved dexterity for the operator relative to the standard bulky mobile barrier, and a floor support system with a modified garment design also attempts the same. However, they are still obstacles to free movement of the operator. Another system of barriers (such as those referred to as radio-protective cabins) around the patient has been proposed, but that appears cumbersome, confining, and inhibitory to operator movement both gross and fine, patient/subject contact, and sterile field operation.

Ceiling mounted barriers around the patient also appear to limit contact between patient and operator, and may make control of a sterile field difficult. One configuration includes a ceiling mounted device, which supports the weight of a lead garment, involving a dolly movable in one linear axis, with or without an extension arm that rotates around a central point on the dolly. Such mechanical configurations are in place for other types of suspended barriers and their motion mechanics may not be well suited for use with something attached to the operator's body since the operator must frequently move rapidly and freely in all three spatial axes. Typically, the operator will walk in unpredictable and rapid patterns over an operating area. One configuration includes the garment being suspended by a simple expansion spring, which will provide uneven forces depending on its degree of expansion occurring with operator motion (due to the nature of its simple spring mechanics). It may also result in harmonic motions that affect operator dexterity. In addition, failure of the spring due to cycle stresses could lead to operator injury. In addition, location of the spring in a vertical direction above the operator could result in limitations due to ceiling height. Integration of the system with the heavy image intensifier monitor screen could further encumber the operator from normal motion.

A discussion of the types of motion performed by operators during their work is relevant. Operators generally stand next to an operating table where the patient is positioned. They often reach over the patient to various parts of the body, and they may lean forward while reaching for items, surfaces, etc. This puts stress on the spine when heavy garments are worn. They may bend or stoop, but rarely is this possible because the workplace containing the patient limits vertical motion. In addition, most procedures involve a sterile field where the operator's hands, arms, and torso (from neck to waist, in the front and sides) must remain confined, so excessive vertical motion is prohibited. Nevertheless, motion in the vertical axis is required to some degree as the operator moves. The operator may move considerably in the x and y plane, which is horizontal and parallel to the floor, by walking or turning their body. The operator thus requires freedom of motion in all three spatial axes.

Overhead cranes have been available for many years and are commonly employed in the materials-handling industry. The following is a description of a bridge crane. A bridge crane includes at least one bridge, and a trolley moving on the bridge, end trucks arranged at the ends of the main bridge to support the main bridge, wheels arranged to the end carriages intended to move along substantially parallel rails substantially parallel to the end trucks. In some embodiments, articulated end trucks provide increased maneuverability for the bridge so as to allow the bridge to rotate or sway, while staying safety attached to the rails. Smaller cranes (such as those to be used to support a load up to 250 pounds) are often operated by workers without the aid of motorized assistance because the crane's movable parts are light enough to be manipulated by hand. Different systems are employed to suspend the load from the cranes, including hoists, balancers, balancing arms, articulating arms, manipulators, and intelligent assist devices.

Tool balancers are currently available and help to suspend tools in the workspace in a manner that provides ergonomic benefits for workers using them. The tool balancer is generally attached over the workspace, and reels out cable from which the tool is suspended. Adjustments may be made to provide a "zero gravity" balancing of the tool at the desired height such that the worker may move the tool up or down within a working range without having to bear a significant portion of the tool's weight. Adjustments may cause the tool balancer to exert a stronger upward force such that the operator must apply a downward force on the tool to pull it down to the workspace and the balancer will cause the tool to pull it down to the workspace and the balancer will cause the tool to rise when the operator releases it.

Tool balancers may be of the spring, hydraulic or pneumatic variety, referring to the mechanism, which provides the force for its operation. A spring tool balancer, such as in one embodiment of the invention disclosed herein, generally contains a coiled flat spring (similar to a clock spring), which is attached to a reel with a conical shape and which serves as the platform for the winding of the cable. The conical shape provides a variable mechanical advantage, which offsets the variance of the force provided by the spring as it winds or unwinds. The result is a relatively constant force on the cable within a definable working range. Safety concerns mainly involve falling objects, strength of the suspension device, strength of the cable, and operator falls. The balancer can be attached to the trolley by its own hook and a safety chain. The suspension device is commercially available at specified maximum loads, which include a wide safety margin. The mounting of the suspension device will be done according to architectural/engineering standards where the present invention is to be utilized.

Tools or other loads may also be balanced by arms that provide torque approximately equal to the weight of the load via various mechanical systems including internal cables and pulleys with springs, pneumatic force, or counter-weights. Such arm systems could be manipulator arms, torque arms, reaction arms, or balancing arms as are known in the art.

Detachment of the radiation protection system from the suspension system will require certain care. A cable stop for cable-mounted garment systems will prevent the hanger from going higher than the set level. Some balancers are equipped with a locking mechanism that prevents motion of the cable during load change or removal. This permits simple removal or exchange while standing at ground level. Alternatively, without activating a locking mechanism, the worker could stand on a step stool and lift the load upwards until it contacts the balancer stop, or until the arm is fully raised to its capacity in the case of an arm system, and then remove the garment without concern for sudden upwards, uncontrolled motion of the balancer cable or arm, and attached system. Alternatively, a weight, which is approximately equivalent to the weight of the garment, could be attached to the hanger, cable, rod, or arm prior to disengaging the garment. This will drop the system and require it to be supported by the worker, who may then disengage it from the hanger. The weight will prevent any upward motion of the components in an uncontrolled manner. The next time the garment is attached, the weight could be removed after secure attachment of the system is confirmed.

For most operations, the protection system need not be detached from the suspension system (e.g. cable, rod, or arm supporting the system). It could be left suspended and moved out of the way of other activities. Another alternative method would involve setting the force on the balancer or pretensioner to be slightly greater than the weight of the garment. Once removed from the body, the garment would then slowly and safely rise up until stopped by the cable stop or other safety-stopping mechanism—such as rotating-joint stops for manipulators, balancing arms, and articulating arms. Upon next use, it could be easily pulled back down into position. Annual inspections of the system may be performed for cable frays, hook lock malfunctions, rotating-joint bearing failures or seizures, movement stops, and/or rail component flaws.

In the event of an operator fall, it is unlikely that the system will contribute to operator harm since in some embodiments the suspension system allows the operator to reach the floor without restriction. In view of the embodiments disclosed herein, the design of the system provides for the safe and quick detachment of the operator from the radiation protection system. The binder system quickly provides engagement/disengagement from radiation protection system as the binding forces keeping the operator in proximity to the radiation protection system would be easily overcome by the forces exerted during a fall.

In the event of malfunction, many support systems are equipped with automatic locking mechanisms to prevent dropping of the load supported by the support system. In the event of actual detachment, the frame supporting the suspended shielding components may be designed such that there are pads positioned over the shoulders of the operator which would gently engage the operator's shoulders to support the weight of the device in the event of a suspension failure. However, this type of malfunction would be rare as it would generally be avoidable with adequate support structure strength and annual inspections of the entire system.

In the event that rapid detachment of the operator from the system is necessary due to emergency, the binding system disclosed herein is designed to provide simple and quick disengagement between the operator and the radiation protection system. As disclosed further herein, a simple hand push or wave or actuation of a switch by the operator or another in various embodiments results in the operator disengaging quickly and safely from the radiation protection system without detachment of the garment from the system. The garment can be left hanging on the system and then moved clear of the patient or stretcher. Likewise, the operator can quickly disengage from, and then reengage with, the system while remaining sterile.

Turning back now to the general problem of radiation, it is evident that operators are often exposed to radiation in the course of their work. The proposed concept, outlined herein, describes a device and technique intended to address many of the aforementioned problems. It provides extensive shielding for the operator: covering a large part of the body. The shielding capacity can be increased with thicker, heavy metal layering, thus reducing a dose to the operator because the device is weightless [or nearly so] to the operator. The device is close to the body of the operator, much like a conventional apron, however it is not supported by the operator. It moves substantially in concert with the operator as he/she moves around within the working field and sterile field, and allows movement of arms and body parts to accomplish the procedure at hand.

The overall effects of the device include: improved comfort for the operator who is no longer supporting heavy-shielding clothing, improved radiation protection to an operator through a much greater portion of body shielding (compared to a conventional apron), as well as more effective shielding of much of the covered parts due to the substantial contour of the garment to the operator and thus better use of the shielding material. This approach also offers a musculoskeletal benefit due to the absence of a significant weight burden on the operator.

Figure 2:
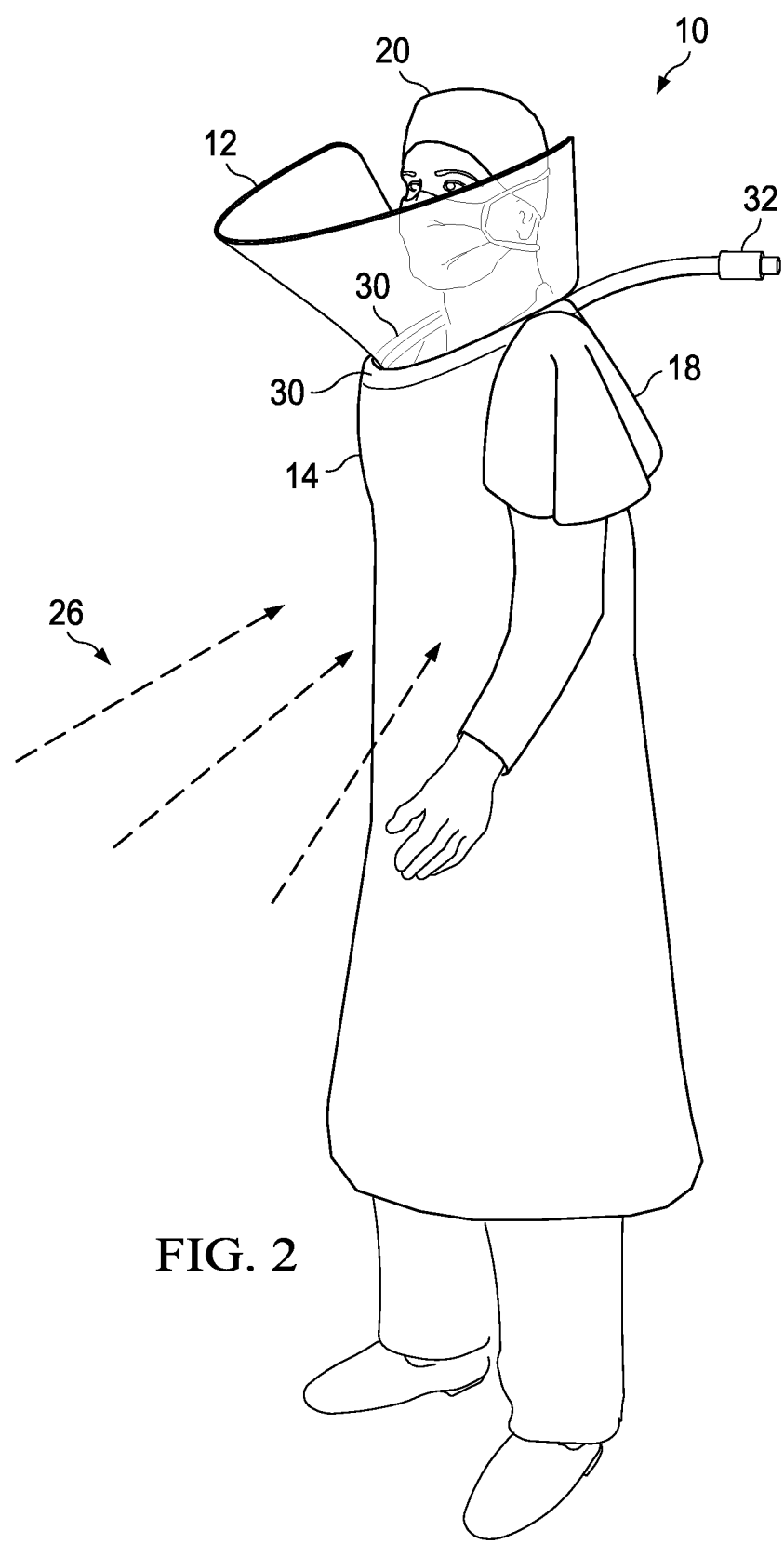
FIG. 2 is a perspective view of a personal radiation protection system in accordance with the present invention.

FIG. 1 is a perspective view of one embodiment of a suspended personal radiation protection system 10, which is shown in greater detail in FIG. 2, where a rigid, substantially vertical suspension component 24 of a ceiling-mounted articulating arm 22 is used to directly attach to a radiation protection garment 14, in accordance with the present invention. System 10 may also include an operator 20, a patient 28, a radiation source 16, radiation rays 26, a suspension component 22, and frame 30 for supporting a radiation protection garment 14. The system 10 may also include a face shield 12, and an arm hole sleeve cover 18. Each of these components is discussed in further detail herein.

In general, and as illustrated in FIG. 2, the garment 14 is suspended from a frame 30 which is in turn supported by a given suspension component. In one embodiment, hanger 32 is attached to frame 30 (or "garment frame"), which is the skeleton that contours around the shoulders, chest and torso of the operator 20. Frame 30 supports garment 14 and face shield 12, along with other devices such as an instrument tray, environmental control (e.g. a fan, a heater, an air conditioning device) and/or lighting apparatus. Frame 30 may be integrated—rigidly or with articulation—with hanger 32, or may be attached directly to the suspension component as required by operational mandate. In one embodiment, hanger 32 is a rigid rod that connects frame 30 to the desired suspension component, such as a reaction arm, balancing arm, a manipulating arm ("manipulator"), an articulating arm, any number of wire ropes, or any other suspension component described or envisioned herein. Attaching frame 30 to a suspension system over the operator's head, and roughly over the center of gravity, can have advantages for facilitation of balance and proper orientation of the device. Alternatively, attaching frame 30 in any other location, such as behind (as depicted in FIG. 2) or to the side of the operator 20, can offer advantage with regard to positioning of the suspension system in an alternate location, other than overhead the operator 20, for better function in some environments.

FIG. 2 further illustrates the system architecture by a perspective view of a personal radiation protection system 10. An operator 20 may position herself in relative proximity to the garment 14 and frame 30 such that the operator 20 is not supporting the weight of the garment 14. In this sense, she is liberated from the typical and problematic weight constraint. While using radiation 26 during a procedure or task, the operator 20 can freely move in the X, Y and Z spatial planes such that the garment 14 and face shield 12 are substantially weightless. Garment frame 30, or when coupled with hanger 32, can lead upward from any portion of the garment system 10 to attach to an overhead suspension system such as a bridge system or reaction arm. Alternatively, frame 30, or when coupled with hanger 32, can lead to the suspension system in a non-overhead location by passing rearward, and/or to the side of the operator 20, as shown. Some embodiments of the invention depicted may also utilize a gimbal, end effector, or other type of articulation within the frame 30 or hanger 32, close to the operator 20 or near the center of gravity of the system 10 to facilitate certain movements, as described later herein. The rearward or sideward frame component 30 may arise at other levels of the operator 20 other than the shoulder, such as closer to the waist, or midway between shoulder and waist, or possibly lower.

FIG. 3 is an elevated side view of the manipulator-arm-type, or reaction-arm-type, garment suspension system 40 seen in FIG. 1, in accordance with the present invention. A manipulator arm suspension assembly 40 allows the operator to move freely in the X, Y, and Z planes while maintaining proximity to and protection by the protection system. Suspension system 40 includes a post 42, which, in this embodiment, is attached to a moveable system consisting of ceiling rails and a trolley on wheels as depicted in FIG. 1. Post 42 alternatively could be attached to a fixed point, such as a wall or ceiling. A first arm 46 is attached to the post 42 such that the first arm 46 may rotate about a rotating first joint 44 in a planar fashion. A second rotatable arm 52 is attached to the first arm 46, and is also operable to rotate about a rotating second joint 48 in the X, Y plane and to rotate about a rotating third joint 50 in the Y, Z plane. The second and third joints 48, 50 may alternatively be combined into a single ball-and-socket (or "ball-and-cup") joint to provide rotation in the X, Y, and Z space. A third arm 58 is operable to rotate about a rotating fourth joint 54 and a rotating fifth joint 56 in various planes relative to the second arm 52. Similarly, the fourth and fifth joints 54, 56 can be combined into a ball-and-socket joint. The joints connecting each of the arms described above are well known in the art and may consist of friction joints, torque joints or substantially frictionless connection joints using well-known means such as bearings or bushings.

In this particular embodiment, arm 52 contains a linkage system (not depicted) that maintains the orientation of third arm 56 in the vertical axis, perpendicular to the first arm 46. As fifth joint 56 allows rotation in only 1 vertical plane, instead of infinite vertical planes as with wire rope, the remainder of the arm will more responsively follow the operator as he or she moves, starting and stopping in concert with the operator. In contrast, with wire rope suspension systems, the rope will first angle before pulling the arm, which may then give some undesirable backlash effect as it passes over the operator in a delayed manner, and comes to rest after the operator.

The depicted device may also contain (not shown) an internal spring and cable mechanism that acts upon joint 50 between second arm 52 to first arm 46 to maintain an upward force of the suspended protection system approximately equal to its weight. It may have friction built into the joints so that there is some difficulty moving them, and then when the operator releases, the systems remains. In an alternative embodiment, the joints could be substantially free of friction to allow more fluid motion while working.

FIG. 4 is an elevated side view of an alternative suspension component (which can be used in place of the articulating/manipulator arm 22 depicted in FIG. 1) comprising another embodiment of a reaction arm 60, in accordance with the present invention. Arm 60 is a type of articulating arm that can provide a predetermined amount of upward force to counteract the force of gravity that acts upon the desired tool or load to be attached at the end of the arm 60. A reaction arm (or torque arm) with parallelogram construction (i.e., dual, parallel hinged arms acting as one unit), such as that depicted, can allow translation in the X, Y, and Z space of the suspended load, while maintaining the load's pitch orientation. Parallelogram construction maintains effector pitch orientation even in the face of opposing torque forces that would otherwise result in rotation of the object (i.e. undesirably changing its orientation in the YZ plane).

Figure 12:
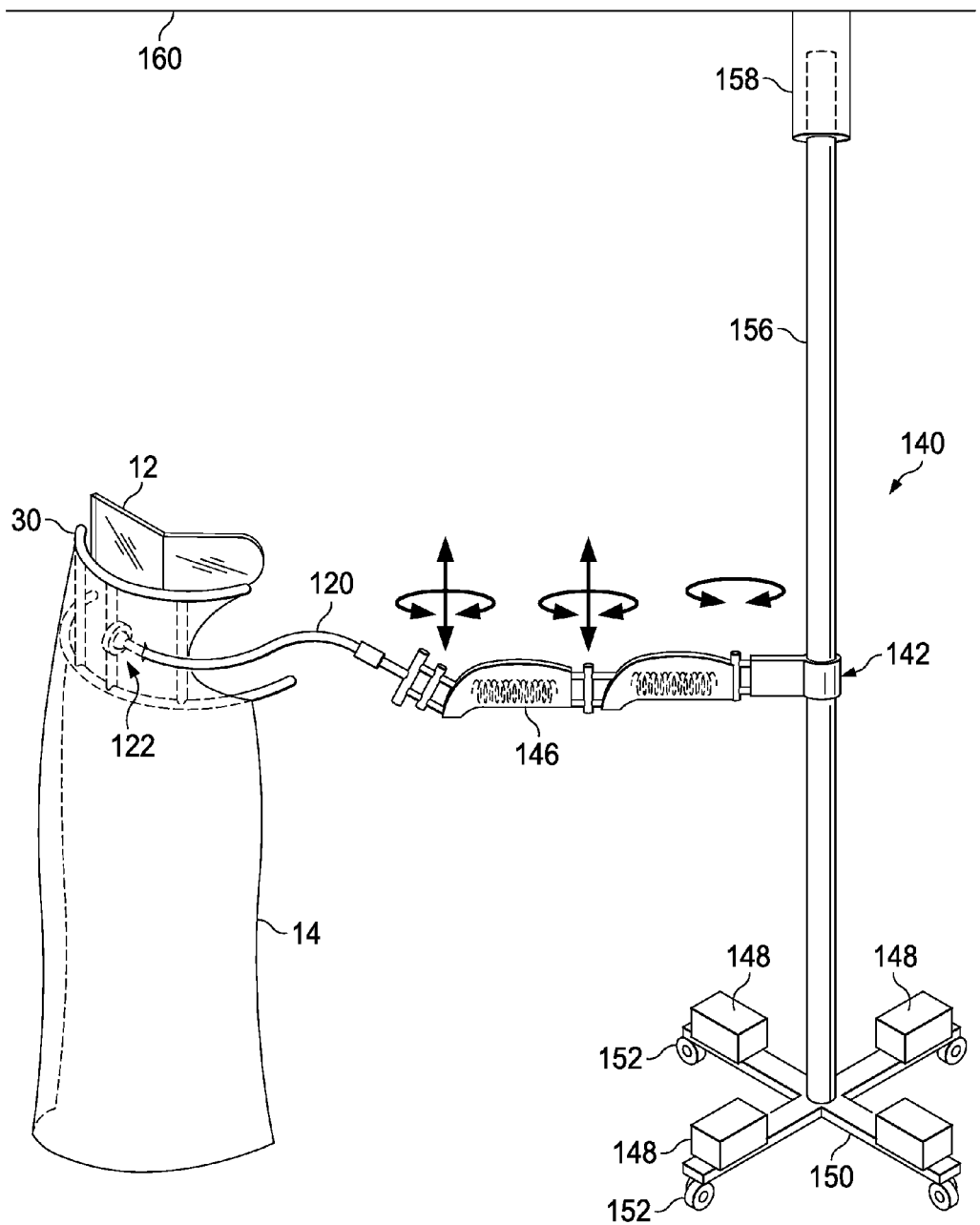
FIG. 12 is a perspective side view of the portable, floor-based, non-overhead suspension system of FIG. 10 modified for ceiling-based docking, in accordance with the present invention.

Balancing arm 60 shown in FIG. 4 is a heavy duty articulating arm with two boom or arm sections 66, 76 extending serially, via rotating joints 64, 68, 74, 78, from a mounting post 62. The mounting post 62 can extend upward to attach to the ceiling or a ceiling-mounted structure, such as the trolley and bridge crane assembly shown in FIG. 1. Alternatively, the mounting post 62 can extend downward to attach to the floor or a floor-based stand, such as any one of the examples shown in FIGS. 10, 11, 14, and 15. The mounting post 62 can even extend from floor to ceiling, as can be seen in FIG. 12.

Returning to balancing arm 60 of FIG. 4, the first boom (or arm) section 66 rotates in a horizontal plane around mounting post 62 via a first joint 64. Second boom 76 also can rotate in a horizontal plane about a second joint 68 located at the end of first arm 66 opposite mounting post 62. Second boom 76 is also capable of rotating (tilting, swinging, or swiveling) in a vertical plane about a third joint 74. If it is desirable for the load-handling end of second boom 76 to maintain its pitch (i.e. forward/backward angle relative to vertical) regardless of the pitch/tilt of second boom 76, second boom 76 may comprise parallelogram construction (i.e. a pair of parallel arms and end joints). Hydraulic cylinder 72 can be used to provide a weight-counterbalancing force to the end of second boom 76. One end of hydraulic cylinder 72 attaches to a leverage extension 70, which may extend upward or downward from the end of boom 76 next to third joint 74. The other end of hydraulic cylinder 76 attaches to some point along second boom 74 to provide a torque about third joint 74 to oppose the torque caused by gravity on the load-bearing end of second boom 76. A zero-gravity, load-balancing effect is thereby provided for the operator. In other embodiments, many other types of balancing mechanisms or linkages are possible, including the use of cables, springs, and reels in various linkage systems. Other degrees of freedom of motion in various joints can be added or subtracted to provide the necessary freedoms and limitations to fit the working situation.

Figure 5:
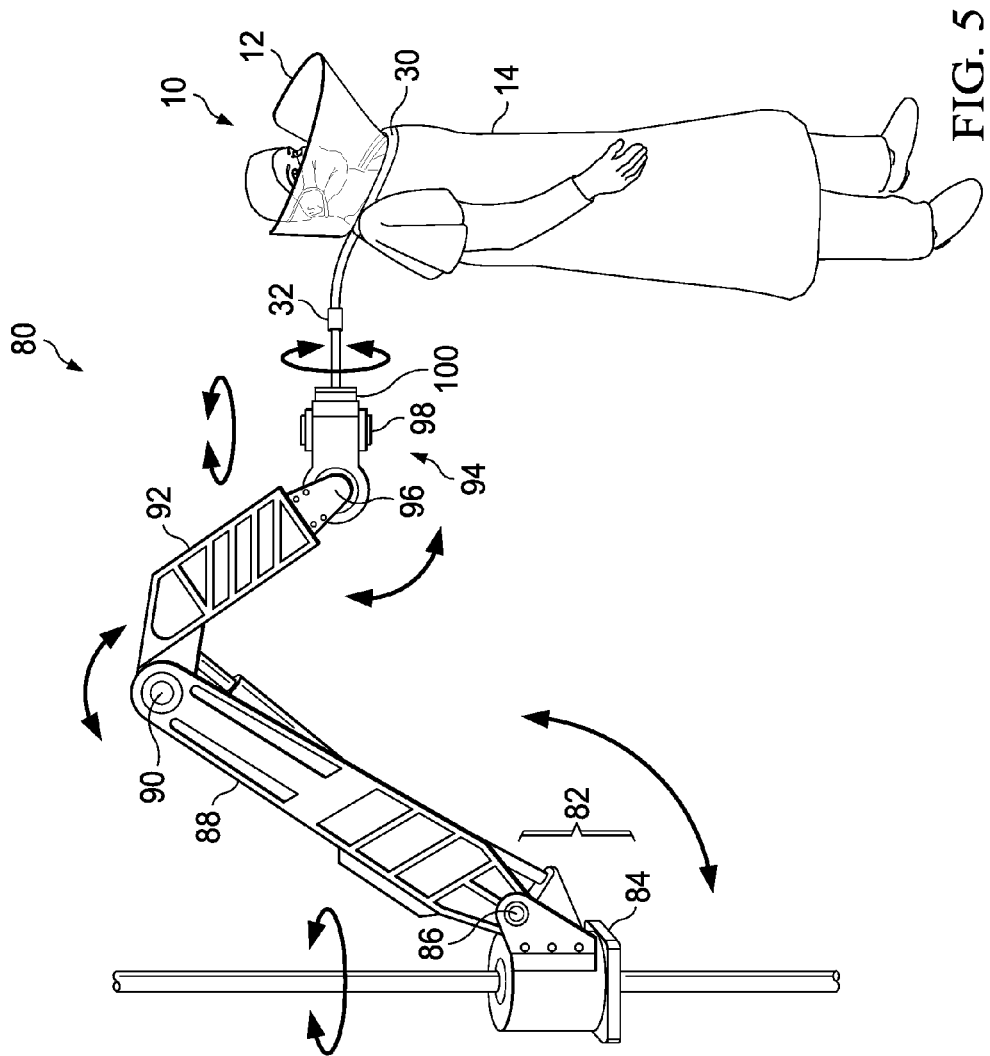
FIG. 5 is an elevated side view of an alternative suspension system with a manipulator arm in accordance with the present invention.

FIG. 5 is an elevated side view of another alternative suspension component comprising a manipulator arm 80 that is holonomic (i.e., having six degrees of freedom) or perhaps even redundant (i.e., having seven or more degrees of freedom), where the manipulator arm 80 has a rotatable pitch axle wrist having at least three degrees of freedom for supportive attachment to the frame 30, in accordance with the present invention. A redundant or at least holonomic manipulator 80 is particularly advantageous because its range of motion and flexibility of orientation approximate those of the human arm.

A human arm is considered to have seven degrees of freedom: a shoulder gives pitch, yaw, and roll; an elbow provides pitch; and a wrist allows for pitch, yaw, and roll. While three degrees of freedom enable positioning in three-dimensional space, additional degrees of freedom are needed to adjust the orientation (pitch, yaw, and roll) of the end effector (or hand). Three degrees of freedom in the manipulator arm shown in FIG. 5 enable the positioning of the end effector at any location in space (defined, for example, by X, Y, Z coordinates). The shoulder portion 82, which comprises a rotatable base 84 and a shoulder pitch joint 86, provides yaw and pitch motion to the manipulator 80. The rotatable base 84 enables rotation or yaw about an upright post for securing the manipulator 80 to a stable point above and/or below the manipulator 80 (such as to an overhead bridge and trolley as seen in FIG. 1, or to a floor stand such as that shown in FIG. 10, 11, 14, or 15). The shoulder pitch joint 86 enables an upper arm portion 88 of the manipulator 80 to tilt or pitch upward or downward. A lower arm (or forearm) portion 92 connects to the end of upper arm 88 via an elbow joint 90, which also allows for upward and downward pitch. At the opposite end of lower arm 92 is a robot wrist portion 94, which is rotatable about a wrist pitch joint 96. The robot wrist (or mechanical wrist) 94, which is shown in more detail in FIG. 6, provides an additional three degrees of freedom for orienting the end effector to a desired pitch, yaw, and roll.

To help provide a zero-gravity-like environment for the shield 12 and/or garment 14 at the end of the manipulator arm 80, a hydraulic cylinder can span between the upper arm 88 and lower arm 92 to apply a counterbalancing torque about the elbow joint 90. A hydraulic cylinder can similarly span between the lower arm 92 and the wrist 94 to provide counterbalancing torque about the wrist pitch joint 96.

In the depicted embodiment, frame 30 can attach to the wrist 94 of the manipulator arm 80 (via a hanger 32, if desired). To facilitate the ease of manipulating and orienting the shield/garment 12, 14, the hanger 32 is more preferably located as close as reasonably possible to shield/garment's center of gravity. This concept will be discussed in further detail in the description of FIGS. 7-9. If desired, a seventh degree of freedom can be provided to the manipulator arm system by using a manipulator hand 102—connected to the end of the wrist 94 that is capable of surge (i.e. extending forward and retracting backward). The hanger 32 and/or frame 30 may be made considerably shorter, allowing the robot wrist to be much closer to the operator, or closer to the center of gravity of the radiation protection system. This may provide more facile fine movements of the operator during pitch, roll, or yaw of his body. This may also be provided by altering the shape of the frame handle 30 or frame 32. Alternatively, additional joints of various configurations and functions may be placed within hanger 32 and/or frame 30 to provide additional degrees of freedom and means for connection to the manipulator arm 80.

Figure 6:
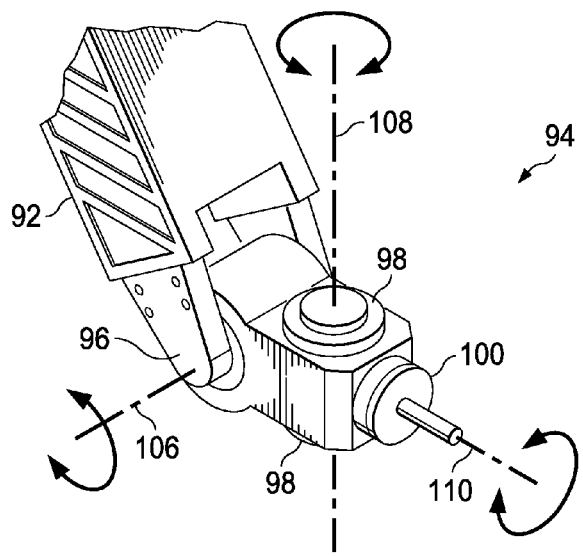
FIG. 6 is a perspective view of the wrist of the manipulator arm seen in FIG. 5, in accordance with the present invention.

FIG. 6 is a perspective view of the wrist 94 of the manipulator arm 80 seen in FIG. 5, as well as the three perpendicular axes of rotation 106, 108, 110 for its three rotating joints 96, 98, 100, in accordance with the present invention. The wrist portion 94 of the manipulator arm 80 provides three degrees of freedom and approximates the flexibility of a ball joint (and the flexibility of the human wrist) by combining three perpendicular joints in a relatively compact space. The wrist pitch joint 96 connects the lower arm 92 to one end of the wrist 94 and has a horizontal axis, which enables the wrist 94 to tilt upward and downward, thus providing pitch. A wrist yaw joint 98 is located in the middle of the wrist 94 and has an axis orthogonal or perpendicular to that of the wrist pitch joint 96, thus providing yaw. At the wrist end opposite the wrist pitch joint 96 is a wrist roll joint 100. The wrist roll joint 100 comprises a rotatable base for providing roll. The wrist roll joint's rotational axis 110 is orthogonal or perpendicular to the axes of rotation 106, 108 of both the wrist yaw joint 98 and the wrist pitch joint 96.

The closer in proximity that each of the wrist joints can be to one another, in the closer the wrist will be to behaving similarly to a spherical wrist. A spherical wrist is where the three axes of rotation actually intersect. Note that in the particular embodiment shown in FIG. 6, although the wrist yaw axis 108 and the wrist roll axis 110 do intersect, the depicted wrist 94 is non-spherical because the wrist pitch axis 106 and the wrist yaw axis 108 do not intersect. Spherical wrists (compared to non-spherical wrists) can be more compact and can reduce the degree of manipulator arm movement necessary to re-orient the shield/garment while maintaining the shield/garment's current spatial position. Non-spherical wrists, however, can be mechanically simpler and more robust.

In order to provide proper balance of the radiation protection device and orientation in space, some of the joints permitting some of the degrees of freedom of the robot arm and wrist may include balancing systems to counteract the effects of gravity on the arm components and the radiation protection device, to render it substantially weightless. Such counterbalancing mechanisms will usually be used to counteract motion in the Z axis (vertically, due to gravity) but may also be incorporated to some degree in the other axes to accommodate the intended circumstances of usage. For example, counterbalancing may be employed in the pitch joint of the wrist, and in vertically moving joints in the arm. The counterbalancing mechanisms may be comprised of any type of system known in the art such as a pneumatic system, simple springs, complex springs, counterweights, or systems of cables and springs with reels.

FIG. 7 is a block-diagram functionality-sketch—with four sub-FIGS. 7A, 7B, 7C, and 7D—of the center-of-gravity garment attachment concept, where side views 7A, 7C and frontal views 7B, 7D are offered of an axle-based and ball-in-cup-based suspension system, in accordance with the present invention. Previous discussions have focused on the suspension of the shield/garment device from the upper portion of its frame. Now we will expand upon suspension mechanisms that are in close proximity to the center of gravity of the shield/garment device in order to improve its motion with regard to certain operator motions such as bending forward or sideways.

When a heavy object is suspended near its top (the point farthest from the earth and its gravitational pull), that object will not easily bend or tilt because such changes in orientation require forces in partial opposition to the gravitational forces. An operator may wish to partially bend over sometimes, as when leaning over the patient table a bit to reach for something. The operator would encounter the forces described, inhibiting the motion somewhat, although not preventing it. It is desired to limit these forces and render the shield/garment system easily tilted and/or bent (or creased or folded). This difficulty can be alleviated by suspension about an object's center of gravity or by a point near its center of gravity.

Figure 7A:
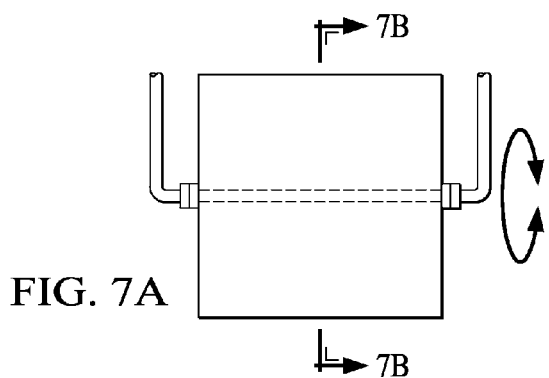
FIGS. 7A-7D depict the functionality of the center-of-gravity attachment mechanism in accordance with the present invention.
Figure 7B:
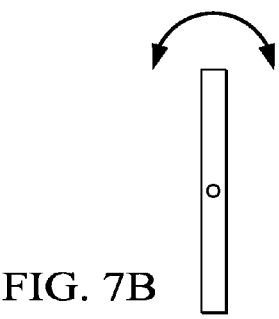
Figure 7C:
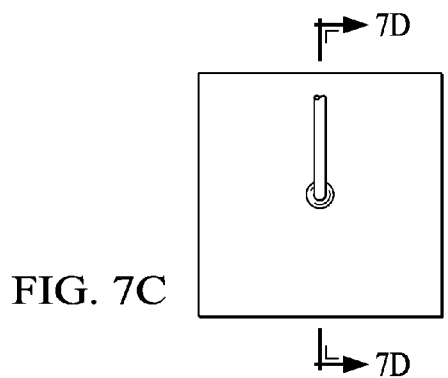
Figure 7D:
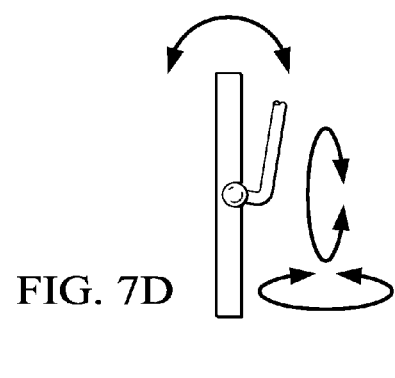

One way to address this is to attach the suspension mechanism to the shield/garment system at its center of gravity. Depending on the type of joint used, this can lead to great ease of tilting or bending in some or all directions because gravitational forces are cancelled out, and the only force required is the minimal force required to overcome friction and accelerate the object into motion. To prevent unwanted free rotation, friction at the joint may be incorporated to desired level, and/or the device can be suspended at a point slightly above the center of gravity so that it tends to orient itself vertically but still requires only minimal force to rotate it. In FIGS. 7A-7O, a typical suspension assembly is shown for the support of a load, which includes an axle system shown in FIGS. 7A and 7B, and a pivot system shown in FIGS. 7C and 7D. Such a system may be a rigid structure such as a rod (shown) or a flexible structure such as a wire rope. Flexible wire rope would allow more freedom of rotation in the YZ plane, which can be desirable or undesirable depending on the situation of use.

Figures 8A, 8B:
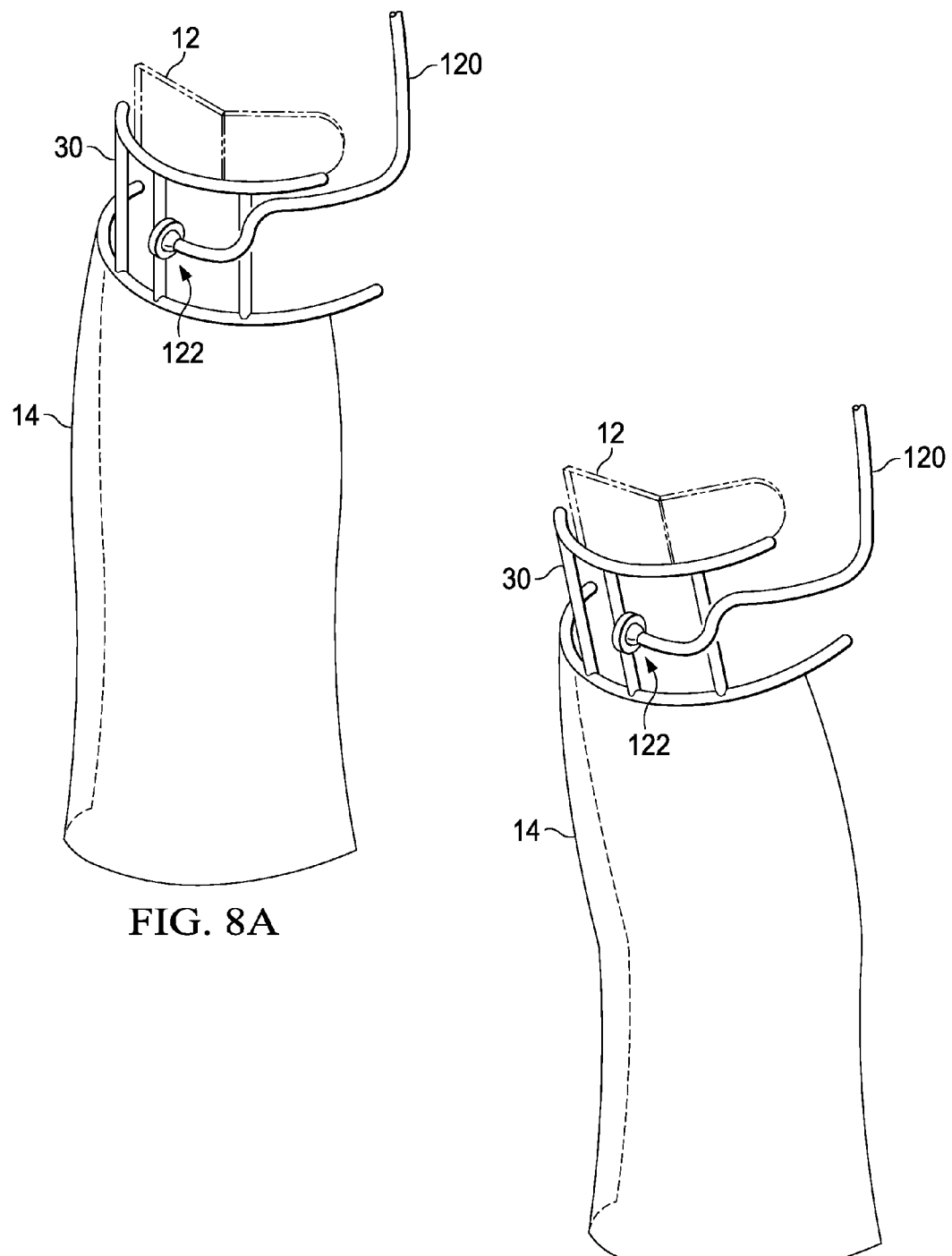
FIGS. 8A-8B offer perspective views of a ball-and-cup center-of-gravity attachment system of the frame to a suspension system in accordance with the present invention.

For example, FIG. 8 offers perspective views of a ball-in-cup center-of-gravity attachment of the frame 30 to a suspension arm 120, with the left perspective view (FIG. 8A) showing the garment 14 in a natural and upright position, and the right perspective view (FIG. 8B) showing the garment 14 in a sideways-bending stance, and where the suspending arm 120 retains the same basic orientation in both instances, in accordance with the present invention. In this embodiment, there is a ball-in-socket joint 122 connecting a rigid suspension arm 120 to the frame 30. The garment portion covering the frame 30 has been removed to depict the frame 30. The center of gravity is high due to the density of the frame and garment making the overall shield/garment/frame system top heavy. By utilizing the ball-in-cup joint 122, the operator can accomplish side-to-side bending and forward bending while the shield 12 and garment 14 remain in proper orientation relative to the operator, and little resistance to these motions is encountered.

The ball and cup joint 122 could be replaced by many different types of joints, such as needle in cup (with needle oriented with a vertical bias, and the cup in a corresponding manner), various manner of bearing or bushing joints, a universal type joint, an axle configuration, or a simple flexible connector such as a wire rope or strap which would permit forward bending. In the event that the center of gravity is located behind the front of the garment 14, possibly at a location that is extremely close to the operator's chest or torso, or perhaps within the operator's body, then it would not be feasible for an attachment at that exact location. However, several practical solutions are possible that permit iso-gravitational freedom of rotation in all planes. Likewise, a counterweight could be added to change the center of gravity forward to a more practical location for attachment. The counterweight would be integrated with the frame 30 in a manner to accomplish this goal, and could be placed as an extension of the frame 30 in any direction to increase moment arm of the counterweight, thus permitting a lighter counterweight to be used. The attachment could be as close as practical to the center of gravity. It does not need to be exactly at the center of gravity, because by being close to it, the forces required to tilt the device would still be minimal, especially since the overall weight of the device is expected to be less than 40 lbs.

As another example embodiment, FIG. 9 offers perspective views of axle-based center-of-gravity attachment of the garment frame to a suspension component, with the left perspective view (FIG. 9A) showing attachment via unilateral axle, the next perspective view (FIG. 9B) showing attachment via bilateral axles and swiveling hanger, the next perspective view (FIG. 9C) showing attachment via bilateral axles, and the right schematic view (FIG. 9D) showing the wire ropes replaced with a rigid frame whose top portion is described by an arc with its center at the center of gravity, at the level of the pivot joints, in accordance with the present invention. An axle system could be employed to provide attachment location at the center of gravity in the Z axis (vertical). As seen in FIGS. 9A and 9B, this would therefore allow excellent forward bending function, without facilitating sideways bending, which may be less important or even undesirable in some situations. The axles could be located at the side(s) only, without running through the center where the operator's body may be located. Another option could be to place suspension components on both sides, such as wire ropes 130 (FIG. 9C), or rigid frame (FIG. 9D), which could be looped or passed over an overhead pulley to provide sideways bending function with great ease. The axle joint could be a simple shaft-in-bearing housing allowing only rotational motion of the shaft, like a bicycle wheel axle. This would allow a unilateral suspension arm configuration which could allow pitch while preventing roll as might be desired in this configuration to maintain proper orientation of the device. Instead of an axle, any type of rotating joint allowing rotation could be used.

Figure 9A:
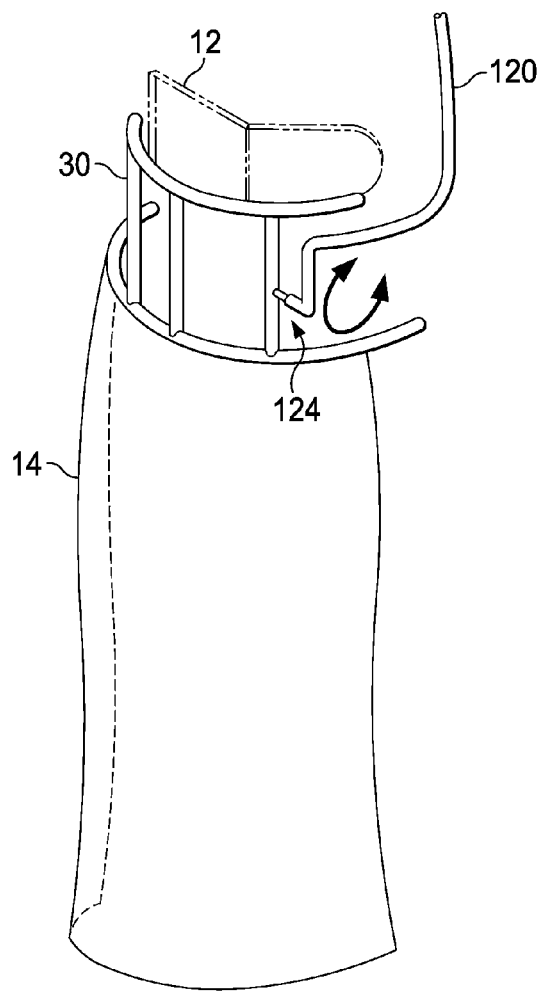
FIGS. 9A-9D offer perspective views of axle-based center-of-gravity attachment of the frame to various embodiments of alternative suspension components in accordance with the invention disclosed herein.
Figure 9B:
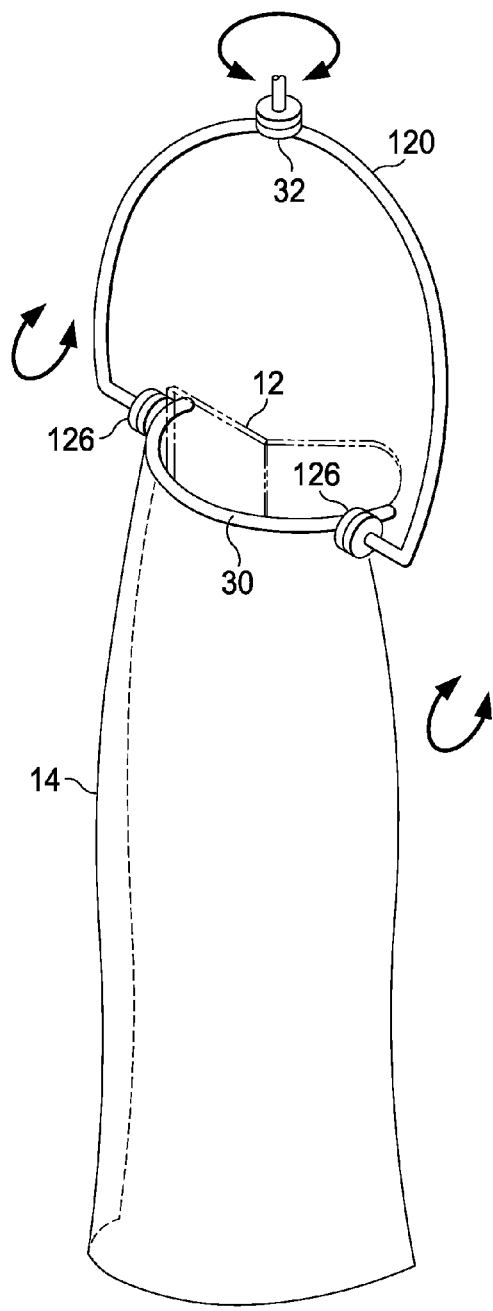
Figure 9C:
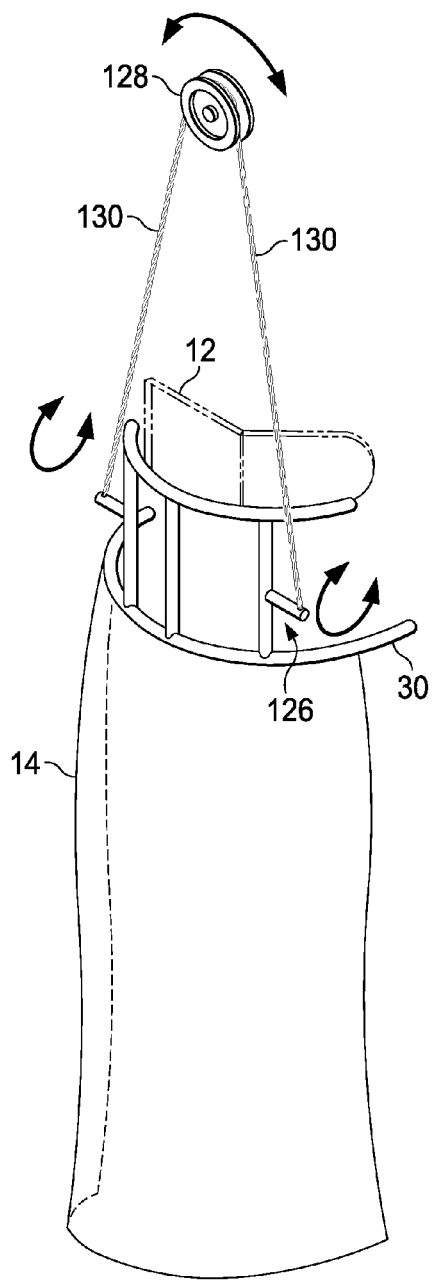

On the left in FIG. 9A, the unilateral axle 124 is at the height of the center of gravity, but it is suspended just left of it. This would allow easy forward bending for the operator, but sideways bending would not be markedly facilitated. In FIG. 9B, bilateral pivots 126 are present slightly above and to the left of right of the center gravity of a frame 30 with a different shape. This allows similar function as the embodiment shown in FIG. 9A, but with the option for using less bulky and strong unilateral support members. A pivot joint rotating in the horizontal plane is integrated with the hanger 32, enabling yaw in the system allowing the operator to twist his body along with the system. In FIG. 9C, bilateral attachments 126 to frame 30 at or near the center of gravity may be rigid since they are connected to wire ropes 130. They do not need to rotate as axles if the wire rope attachment allows rotation. The pulley system 128 overhead allows the system to bend sideways. Yaw would be enabled by flexibility in the wire rope, or the placement of a rotating joint above the pulley that allowed its rotation in the horizontal plane, similar as that depicted in FIG. 9B. This embodiment has somewhat similar function as the ball-and-cup joint at the precise center of gravity, without the need for placing a joint at or near the point of the center of gravity for the system, which may lie within the operator's body or otherwise inaccessible.

Figure 9D:
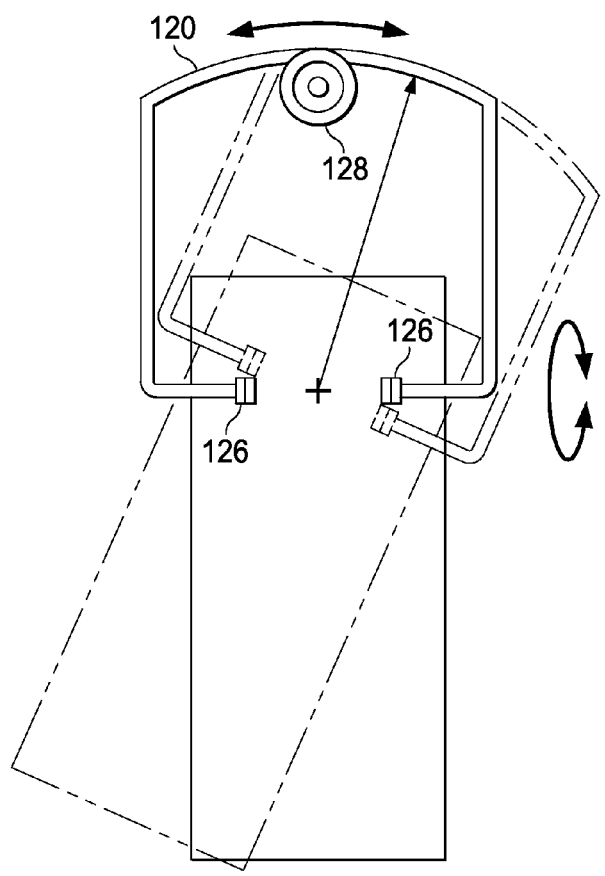

In another embodiment shown in FIG. 9D, wire ropes are not used. Instead, a rigid hanger frame 120 may slide on a pulley. The hanger frame 120 includes an arc whose center is coincident with the center of gravity for the system, thus free rotation (roll) is allowed with very little force or change in weight bearing by the pulley 128. Not shown in this schematic are possibilities that facilitate its use, such as shaping of the lower hanger component to accommodate arm movement. The vertical component of the hanger may have many different shapes to facilitate fit and function, so long as the top arc is defined by its center at the center of gravity, and its highest point is directly over the center of gravity in the vertical Z axis. The pivot joints 126 allow pitch, the pulley 128 and arc hanger frame 120 allow roll, and yaw can be enabled using a pivot above the pulley as previously described, giving full ability to rotate about the center of gravity in all planes.

When using a harness and binding system as described previously, the binding components may benefit from being placed at the same height as the center of gravity attachment. This will facilitate the linkage between operator and device with regard to bodily motion in the XY plane, such as with walking forwards or sideways. If the binding components are not at the same level as the attachment at the center of gravity, such motions of the operator will exert forces on the device that are sufficiently large to cause rotation about the attachment site, creating undesirable motions since in this situation, the operator would want the device to remain in its neutral orientation while it followed the operator's body as they walked. This undesirable effect would be more important for ball-and-cup type joints, than for a purely axle- or pivot-type joint as in the FIGS. 9A and 9B, where sideways motion of the operator would not cause roll of the garment as it might with a ball-and-cup. Therefore, these designs could be useful when the operator binding site is not near the center of gravity. In other embodiments, the preferred attachment site may be slightly above the center of gravity of the system, so the device remains in its neutral orientation for most operator motions in the XY plane, but is still amenable to tilting when the operator bends forward or sideways. In addition to the embodiments shown in FIGS. 9A-9D, a simple tether suspension could be used, such as a wire rope attached directly to the system at its center of gravity.

FIG. 10 is a perspective side view of a portable, floor-based, non-overhead suspension system 140 having a mobile floor stand 142 with an upright post 144 and manipulator arm 146 for distal attachment and suspension of a shield/garment 14, via frame 30, substantially about the garment's center of gravity, in accordance with the present invention. For better stability, the mobile floor stand 142 includes weights 148 along a broad wheelbase 150. The wheelbase 150 has locking (or lockable) wheels 152 for securing the base 150 in position on the floor. Also, the wheelbase 150 is constructed of sufficient dimension and properly counterbalanced with sufficient weight to prevent tipping when the balancing arm 146 is fully extended and laden with the shield/garment 14.

Figure 20:
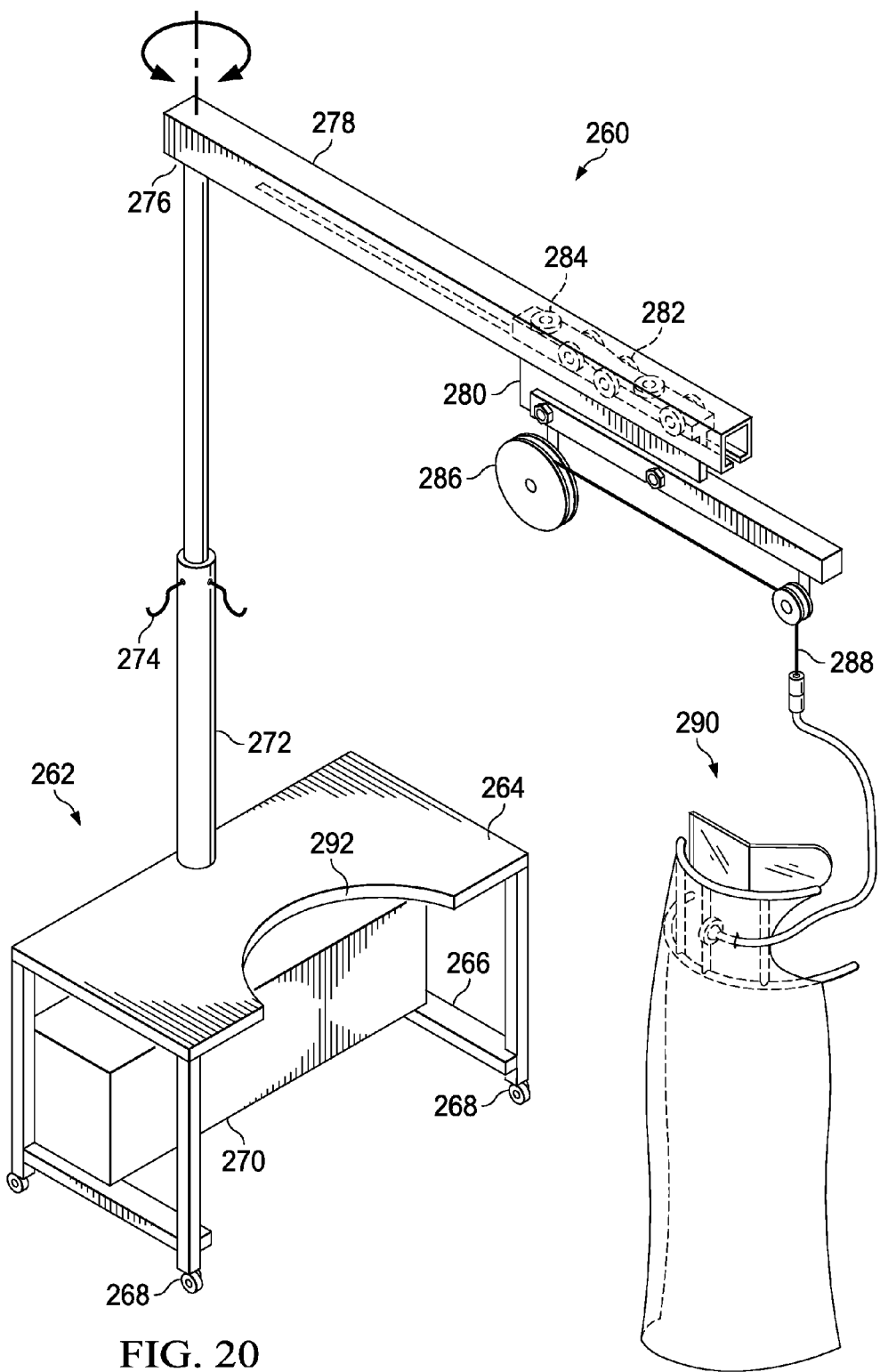

The balancing arm 146 is substantially horizontal and approaches the operator and shield/garment system from the side or back, rather than from overhead. In other embodiments, the arm could approach front the front. In this embodiment, the end effector 120 (end of the balancing arm) approaches the operator from the side at the level of the chest, then curves around the front, and attaches at the center of gravity of the frame of the shield/garment using a ball-and-cup joint 122. This system allows movement of the operator in the procedural area defined by an arc with a radius corresponding to the length of the arm. By putting the stand or mounting system a few feet from the operator, the operator's feet and body are not at risk of accidentally bumping into any part of the suspension system. This offers great advantages over any floor mounted system lacking the ability to distance (via articulating balance arms, for example) the operator wearing the shield/garment 12,14 from the bulk of the suspension system. A modified coat hanger, for example, might be capable of suspending a shield/garment so that the operator is not burdened by its weight. Such a modified coat hanger, however, would be in extremely close proximity to the operator. Without articulating balancing arms to distance the stand from the operator, the operator would be at great risk of inadvertently bumping into or tripping over parts of the stand. This system also offers advantages relative to an overhead floor based suspension system such as seen in FIG. 20, in that the post is not as tall and therefore need not be as wide to manage the same torque forces resulting from the arm and suspended system. Overall weight is reduced, and the system is more portable with fewer overhead collision issues with other apparatus. The system may also be transported through doorways without the need for telescoping posts.

While a ceiling-mounted system (as opposed to a floor-based system) would prevent any possibility of tripping over floor-based suspension components, the floor-based portable system 140 shown in FIG. 10 has advantages over a ceiling mounted system, especially in some specific environments: crowded ceilings are not a problem with this embodiment; the device can be wheeled into different procedure suites in the same institution; there could be some cost savings related to the absence of ceiling mounting, or the need for reinforcement of the ceiling and expensive analysis of structural support; the absence of overhead structures can reduce risk of collision with other structures such as hanging lights, hanging shields, or a moving image intensifier, which is often angled obliquely towards the operator and is located over their head.

Other configurations are possible, including a very short post, or no vertical post, with the arm attached to the wheelbase of the stand and extending upward to the attachment site with the radiation protection system. The arm could also be affixed rigidly to a site on a fixed surface, including the floor, wall, patient table, or stable back table. Also, the arm may attach to the frame with many different types of joints described elsewhere or located in other locations on the frame (e.g. an axle or pivot joint with one degree of freedom on the right side of the frame allowing forward tilt of the operator). The frame could be altered to allow a lower point of connection, by being extended more inferiorly towards the floor.

FIG. 11 is a perspective side view of the portable, floor-based, non-overhead suspension system of FIG. 10 modified for floor-based docking, in accordance with the present invention. By extending downward a floor-docking post or pole 154 from the bottom of the floor stand 142 into a receiving sleeve or channel in the floor or ground, the mobile floor stand 142 can be securely docked in place. The floor-docking post 154 increases the suspension system's ability to withstand torque applied to the end of the balancing arm 146 due to the weight of the suspended shield/garment/frame components 12, 14, 30 by docking the post 154 with this fixed surface. When not docked, the system 140 could be unstable with the arm 146 extended and load 12, 14, 30 attached. To permit undocking and portability without removal of the load 12, 14, 30, a system could be employed involving a locking mechanism for the portion of post 144 docked under the floor level 154, such that it cannot be telescoped back into the base 150 until unlocked. Unlocking would be enabled only when the arm 146 is swung in so that the supported weight is positioned very close to the post 144, thus reducing torque. Once the post 144, 154 is retracted and undocked, the arm 146 would lock so that it could not be extended to make the system 140 unstable. The arm 146 could be unlocked once the post 144, 154 is docked again to this fixed surface. This safety mechanism can be incorporated into each of docking system embodiments described herein. Although FIG. 11 depicts one embodiment of this floor docking mechanism with a non-overhead suspension system, the floor supported system could be utilized with any of the described arm or jib systems, including overhead suspension systems. It could also be utilized with a bridge system where it might offer advantage if a floor-based bridge system were set up in a cantilevered fashion requiring stabilization as could be offered by this floor docking mechanism.

Other types of floor docking mechanisms are possible. Any number of the wheels could be designed to bind or attach securely to components on the floor to provide stability and prevent translational or rotational (tipping) motion of the stand. Other extensions or plurality of extensions from the device could attach as described above for the wheels. The attachments could be rails allowing some degree of motion in some directions. Any type of securable attachment system could be envisaged using mechanisms widely known in the art.

FIG. 12 is a perspective side view of the portable, floor-based, non-overhead suspension system of FIG. 10 modified for ceiling-based docking, in accordance with the present invention. By extending upward a ceiling-docking post or pole 156 from the top of the floor stand 142 into a receiving sleeve (e.g. a ceiling-post sleeve 158) or channel in the ceiling 160 or other ceiling-mounted structure, the mobile floor stand 142 can be securely docked in place. The ceiling-docking post 156 increases the suspension system's ability to withstand torque applied to the end of the balancing arm 146 due to the weight of the suspended shield/garment/frame 12, 14, 30 by docking the post 156 to this fixed surface. The diameter and bulk of the post 156 can be substantially reduced, and the wheelbase and weight of the base may also be reduced relative to non-docking systems. In the embodiment shown, the floor docking mechanism is depicted with a non-overhead suspension system; however, it could be utilized with any of the previously described arm or jib systems, including overhead suspension systems. It could also be utilized with a bridge system where it might offer advantage if a floor-based bridge system were set up in a cantilevered fashion requiring stabilization as could be offered by this floor docking mechanism. Also, floor docking and ceiling docking (fixed surface) mechanisms could be present in the same device.

Other types of ceiling docking mechanisms are possible. Other extensions or plurality of extensions from the device could attach to sites secured to the ceiling. The attachments could be rails allowing some degree of motion in some directions. Any type of securable attachments system could be envisaged using mechanisms widely known in the art.

Figure 13:
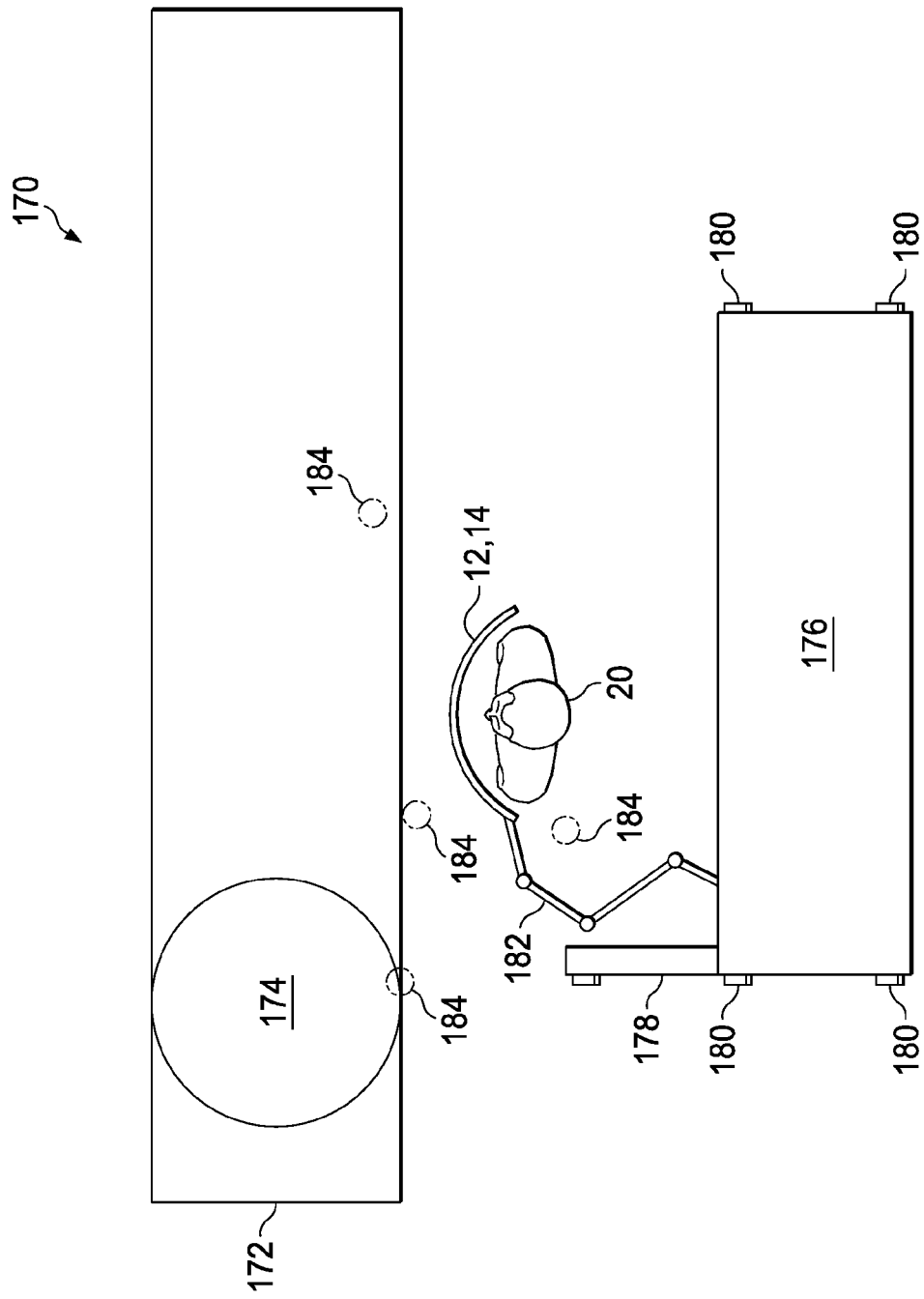
FIG. 13 is a top view of a portable, floor-based, back-table-mounted garment suspension system, in accordance with the present invention.

FIG. 13 is a perspective side view of a portable, floor-based, back-table-mounted garment suspension system with non-overhead suspension 170, in accordance with the present invention. The embodiment shown in FIG. 13 allows for articulated, balanced arm support of the operator's shield/garment by relatively inexpensive modification of commonly used back tables (fixed surfaces). This helps reduce operator fatigue (due to the cumbersome weight of the shield/garment) without requiring the installation of a ceiling-based mounting system, such as a bridge crane and trolley, which can be quite expensive and/or complex, and without having to set aside precious floor space for a dedicated garment-holding floor stand. Such a back-table-mounted (fixed surface) suspension system is portable, therefore it can be easily moved with the back table from one room to the next, or even simply moved out of the way when not in use.

A typical radiological examination room (and/or operating room) has a patient table 172 with an image intensifier 174 at one end of the room (which relative end will be referred to herein as the front of the room). The operator 20 generally works behind or adjacent the patient table 172 while wearing the radiation-blocking shield/garment 12, 14 with his or her back facing the back of the room. A back table 176 is located behind the operator 20 towards the back of the room and is used by the operator 20 to keep his or her tools and/or other equipment within convenient reach. With a few modifications to the typical back table—such as providing extended table legs (or outriggers) 178 for widening the table's base and providing locking wheels 180 and/or floor hooks—the back table 176 can be made stable enough to serve as a secure fixed-surface support platform for a shield/garment-suspending articulating arm and/or balancing arm 182 system. With a few modifications, it is also possible, in the alternative, to mount such a shield/garment-suspending articulating arm and/or balancing arm system at many different possible locations 184 including on the patient table or even to a point on the floor as depicted 184. Although the depicted embodiment is shown with a non-overhead articulating arm, any type of arm or jib system, including overhead or non-overhead, could be modified and used in alternative embodiments.

Figure 14:
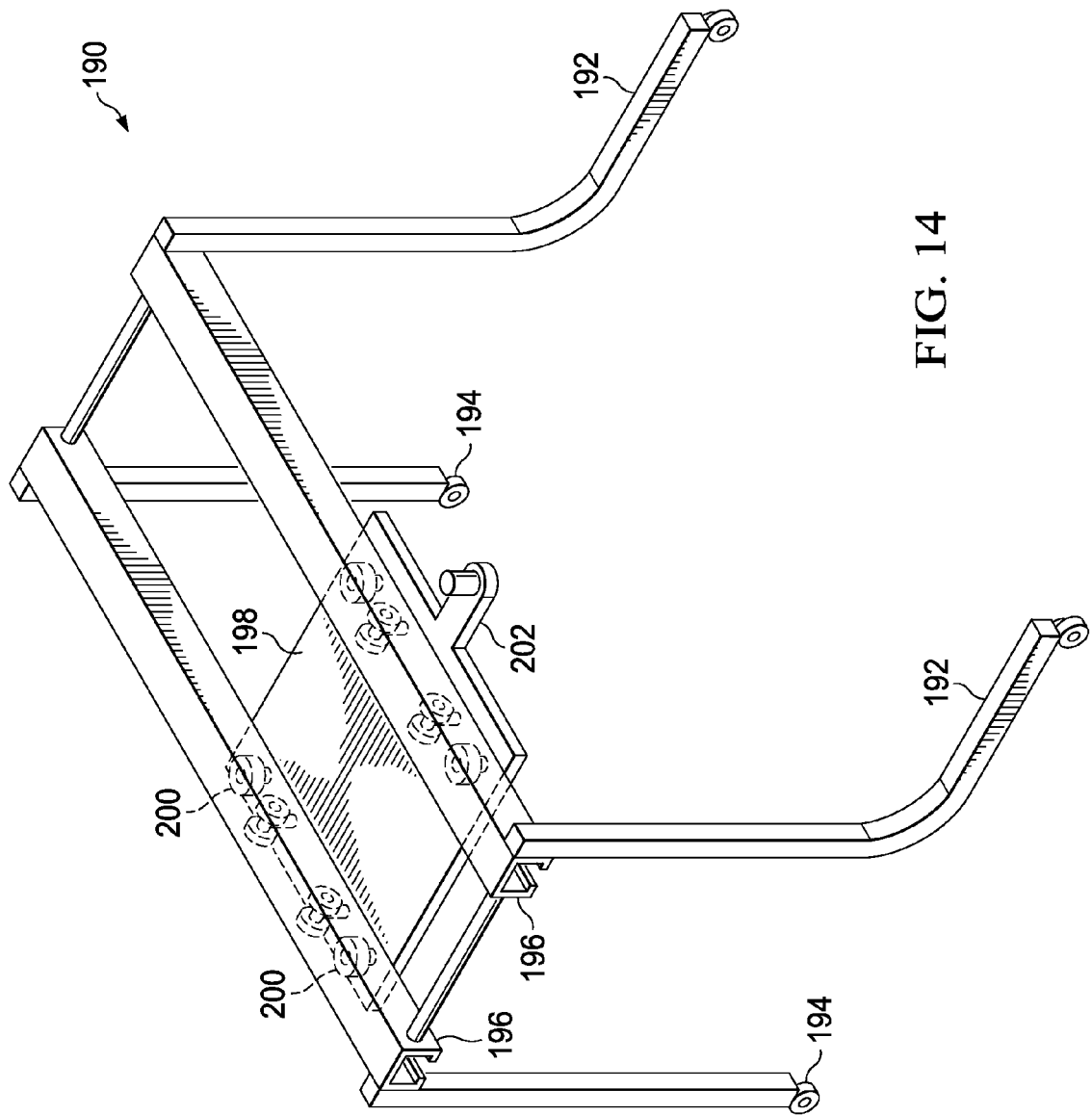
FIG. 14 is a perspective view of one embodiment of a portable track stand for use with the back-table-mounted garment suspension system in accordance with the present invention.

FIG. 14 is a perspective view of one embodiment of a portable track stand 190 for use with the back-table-mounted garment suspension system 170 shown in FIG. 13, where stability is provided by the track stand's broad base 192 and locking wheels 194, in accordance with the present invention. Stand 190 rolls multi-directionally on wheels 194. It contains two track rails 196 that allow a trolley 198 to move longitudinally along the track via trolley wheels 200, while also providing the ability to withstand the moment arm forces produced by the weight of the balancing arm 202 (mounted onto the trolley 198) and shield/garment device (not shown). Trolley wheels 200 may be lockable, so that the trolley can be locked in the desired working position so that further motion during work is only available in the arm system connected to stand 190. The top of the portable track stand 190 may be covered or otherwise modified to simultaneously serve as a back-table.

Figure 15:
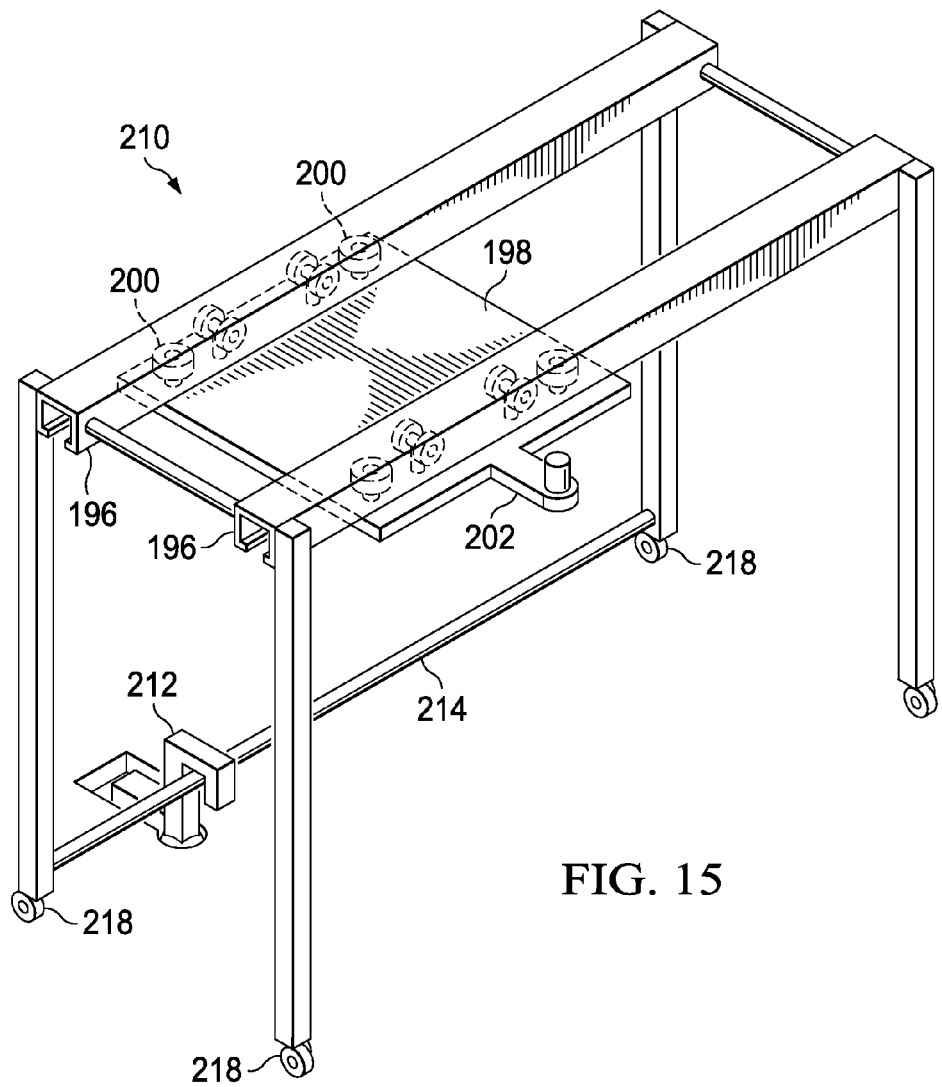
FIG. 15 is a perspective view of another embodiment of a portable track stand for use with the back-table-mounted garment suspension system in accordance with the present invention.

FIG. 15 is a perspective view of another embodiment of a portable track stand 210 (in the depicted embodiment, a floor-locking portable track stand) for use with the back-table-mounted garment suspension system shown in FIG. 13, where stability is provided by at least one stowable, recessed floor hook 212, in accordance with the present invention. In this embodiment of the portable track stand/table 210, there is attached to the floor a mechanism, hook 212, that can attach to and detach from a crossbar 214 along the base of the table 210 using simple operator movements. It stabilizes the table 210 by preventing the backside from elevating due to the torque created by the attached balancing arm 216 and the suspended radiation protection device (not shown). This allows a substantial reduction in weight and/or wheelbase of table for stability purposes and serves to further minimize unwanted lateral motion of the table 210 along the floor that might occur in small degrees even with the wheels 218 locked in place. One or more floor hooks 212 may be used in any of the portable stands or back table embodiments described herein and as required by the operational requirements. Alternative embodiments may provide a locking safety mechanism similar to that described in FIGS. 11 and 12 which only permits unlocking from the floor when a load is stowed over or close to table, and the support arm cannot be extended unless locked to floor.

Figure 16:
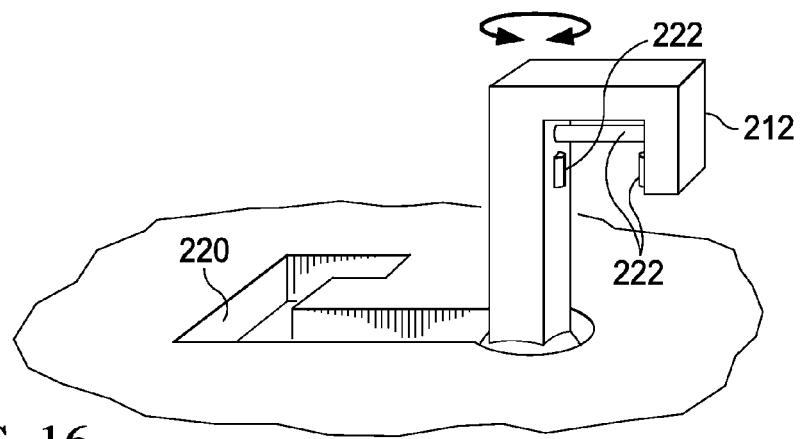
FIG. 16 is a perspective view of one embodiment of the stowable, recessed floor hook in accordance with the present invention.

FIG. 16 is a perspective view of one variation of the stowable, recessed floor hook(s) 212, in accordance with the present invention. To prevent obstruction or tripping of personnel when the floor hook is not being used, the floor hook 212 can fold down into a recess or inset 220 in the floor. To stow away the floor hook 212, the operator might, for example, first rotate the floor hook 212 ninety degrees (90°) counter-clockwise, then fold it down into floor. Once in the floor (i.e. within the correspondingly-shaped floor recess 220), the floor hook 212 would lie flat/flush with the floor without risk of being obstructive. In yet another variation of the floor hook 212, the hook 212 can freely rotate about its floor attachment, allowing the table 210 to change orientation while securely but rotatably held by the floor hook 212 to this fixed surface. The floor hook 212 itself, along its hooking surfaces, can also have top rollers and side rollers ("top" and "side" relative to the table crossbar being hooked) 222 to allow the table 210, while hooked, to shift laterally—from side to side—along the floor (i.e. along its long axis) for increased range.

Figure 17:
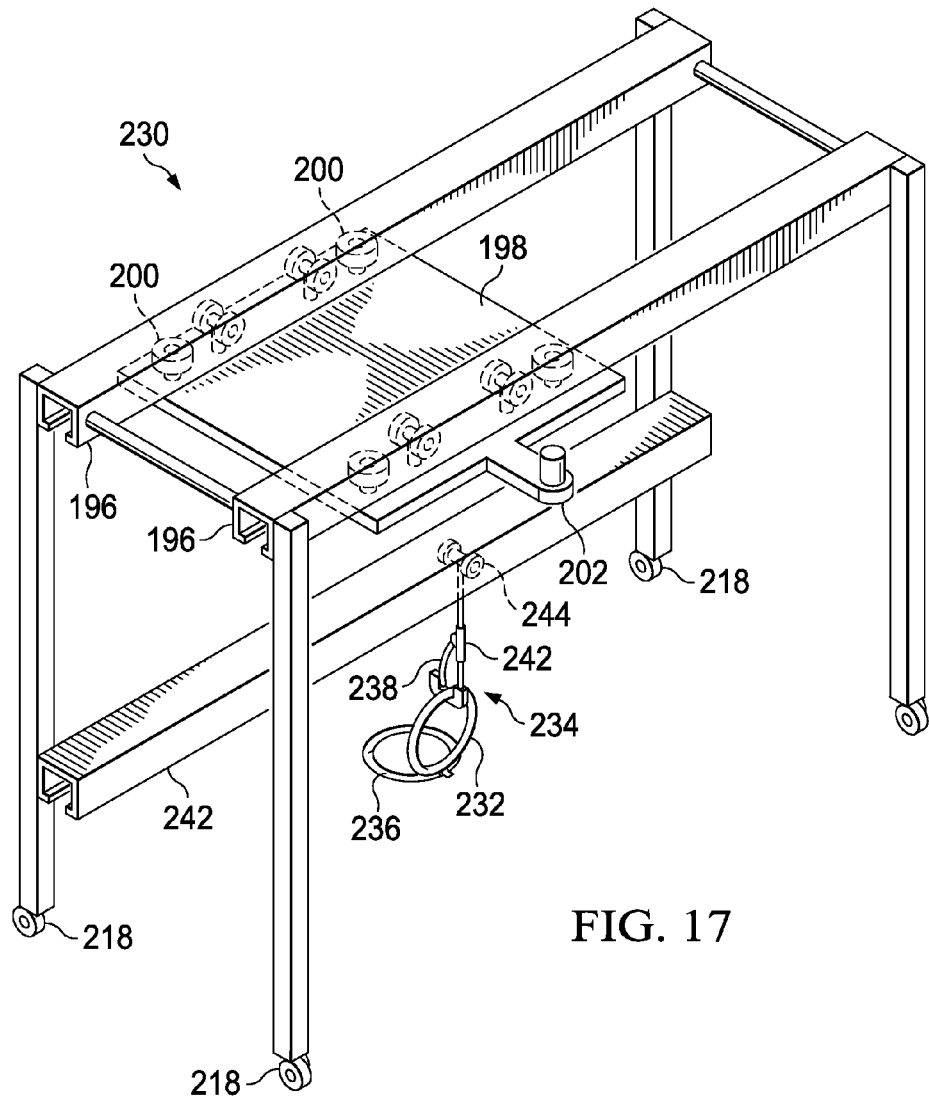
FIG. 17 is a perspective view of another embodiment of a portable track stand for use with the back-table-mounted garment suspension system in accordance with the present invention.

FIG. 17 is a perspective view of another embodiment of a portable track stand 230 (more specifically, a cam-locked portable track stand) for use with the back-table-mounted suspension system 170 shown in FIG. 13, where stability is provided by at least one stowable, recessed floor ring 232 and at least one cam-locking hook (or other cam-locking ring catch) 234, in accordance with the present invention. The floor ring 232 folds up from the floor inset (or recess) 236, and the cam-locking hook 234, which has an operating handle 238 for locking the hook 234 and tightening its hold, attaches to it. The operator squeezes the cam lock handle 238 closed. This action shortens and tightens the apparatus, pulling downward as it locks, to provide sufficient downward pull on the table 230 to prevent it from wobbling or lifting slightly off its wheels when weight is applied on the balancing arm. There is also a length-adjustor mechanism 242 on the shaft of the cam lock 234 to provide coarse adjustment of the length. This mechanism can be supported from a trolley 242 with trolley wheels 244 that can roll freely along the track attached to the legs of the table 230. Such a rail system can be applied to any of the floor-docking table systems described herein. As in previous embodiments, this stand 230 can simultaneously serve as a back-table for procedural supplies by placing a tabletop on it, for example, and covering it with a sterile drape as is customarily done. A joint allowing rotation of the floor ring 232, and/or of the shaft for the cam-lock hook 234 that grips the ring 232, will allow rotation of the table 230 in the plane of the floor with the floor ring 232 as the center of rotation. There can be a safety mechanism to prevent unclamping of cam lock 234 while the shield/garment (or other load) is positioned on the balancing arm 240, as a sufficient torque applied against the balancing arm 240 might undesirably allow the table 230 to tip. To prevent the need to remove the load, the balancing arm 240 and its load could be placed into a parked position where the load is positioned substantially over the center of the table 230.

Figure 18:
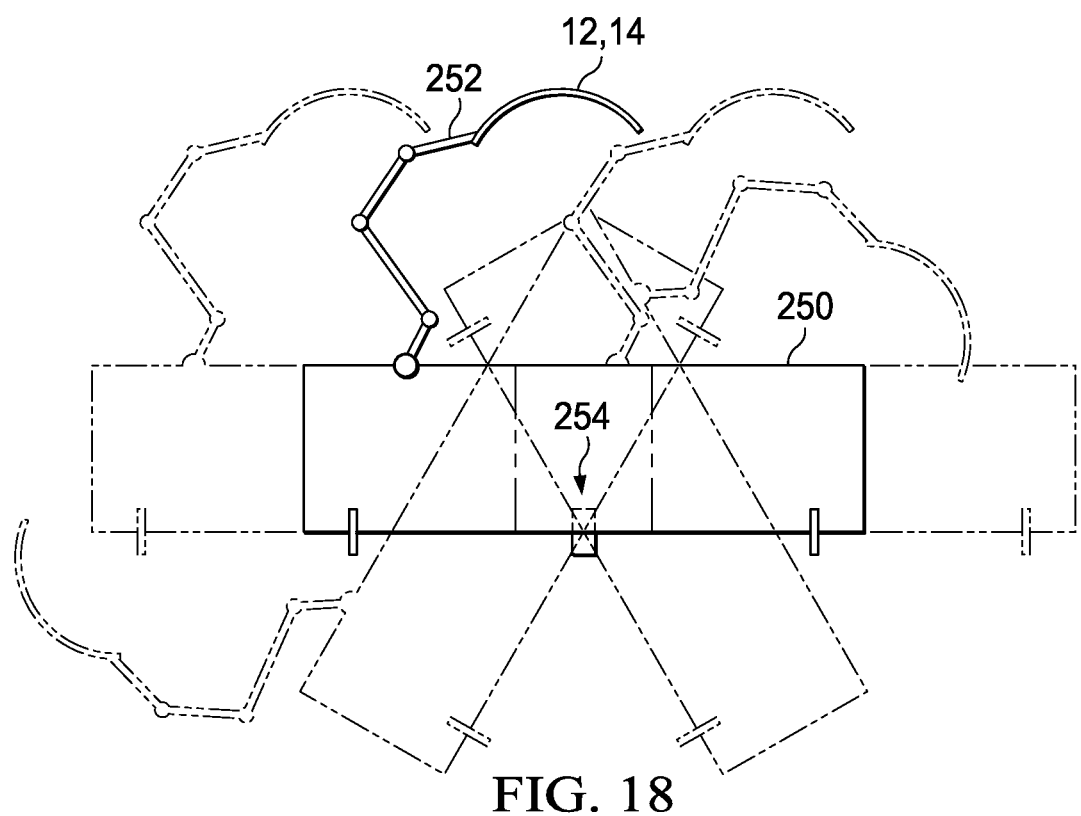
FIG. 18 is a top view of the range of motion available to the portable track stand for use with the back-table-mounted garment suspension system in accordance with the present invention.

FIG. 18 is an elevated top view of the range of motion available to the portable track stand 250 for use with the back-table-mounted garment suspension system 170 shown in FIG. 13 and with the floor-securing means depicted in FIGS. 15-17, in accordance with the present invention. The floor hook 254 is positioned near the middle of the table 250 in the neutral position, hooking the crossbar of the table as previously described. The table can be rolled to the left or right, or rotated around the hook 254 as shown, giving great range to the balancing arm 252 and shield/garment attached thereto.

Figure 19:
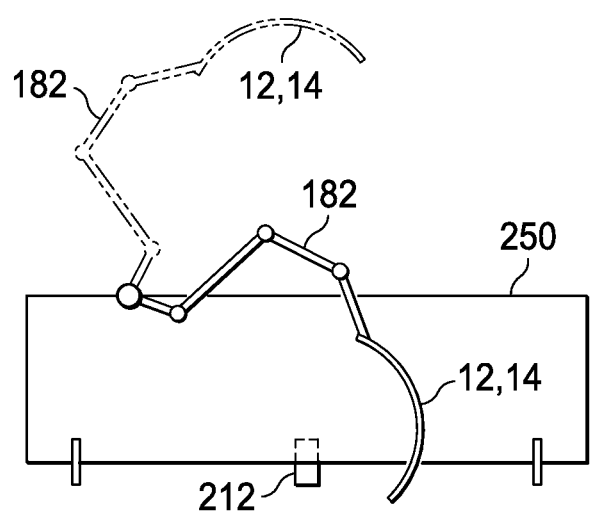
FIG. 19 is a perspective view of the portable, floor-based, back-table-mounted, non-overhead or overhead garment suspension system where an example table-mounted manipulator arm is depicted in an operating position and a parked position, in accordance with the present invention; and, FIG. 20 is a perspective view of the portable, floor-based, back-table-mounted overhead jib system with extension arm on the trolley.

FIG. 19 is a perspective view of the portable, floor-based, back-table-mounted garment suspension system 170 shown in FIG. 13 where an example table-mounted manipulator arm 182 is depicted in two positions: an operating position and a parked position, in accordance with the present invention. The table 176 may be unhooked from the floor when tension is released from the hook mechanism 212, indicating the table 176 is stable. This can be achieved by removing the load, or in this instance, by rotating the load substantially over the table 176 to remove moment arm or torque forces. Another embodiment of safety lock could involve a mechanical linkage between a table-to-floor locking mechanism, and the arm such that the locking mechanism can unlock only when the arm is swung into a safe position where the table is stable without tethering to the floor. The device can swing over or under the table 176. The latter has the advantages of space savings, lower center of gravity, non-obstruction of the tabletop area, and better aesthetics. The garment 14 may be constructed to roll or fold up so that its vertical distance is reduced, allowing the device to park more easily in the space available.

FIG. 20 is a perspective view of a back table 262 combined with a jib arm and trolley suspension for the radiation protection system 260. In this embodiment, a frame 266 on wheels 268 supports a column 272 for a jib-boom system. A table top 264 is connected to the frame 266 and serves as the fixed surface back table 262 for the operator's supplies. Underneath the table top 264 is a compartment 270 containing weights and a motor system to move the system 260 via powered wheels 268. A sterile drape may be placed over the table top 264 as is common in the art. The column 272 may also include hooks 274 for hanging medical supplies or instruments. The column 272 may telescope to change its height, and which may be facilitated with a counter-balance system 286 (of any type, but the use of counterweights may be advantageous to provide more weight and stability) to negate the weight of the upper column 272, boom 278, and suspended components 290 (e.g., garment/shield). A rotating joint 276 between the boom 278 and the column 272 allows rotation of the boom 278 in the horizontal plane. In this embodiment, the boom 278 is telescoping with an integrated trolley 280 with anti-kickup wheels 282 and side rollers 284, although a conventional boom could be used. A trolley 280 has linear motion along the boom 278. The radiation protection system 290 is suspended by a wire (or line) 288, and its weight is counterbalanced by a balancer 286 attached to the trolley 280, and placed rearward for counterbalance advantage in this embodiment. The entire system 260 allows free motion of the protection system 290 in the X, Y, and Z space. The system 260 may be moved into any position in the workplace by the motorized drive and at least two of the four wheels 268 are provided so as to allow steering. The table 262 is deep to create a long wheelbase in the short axis, to increase stability. In this embodiment, the table's front has an arced cut-out 292 to permit more ergonomic usage by the operator despite its deep shape.

System 260 may prove advantageous over a separate floor mounted jib boom and back table because much space is saved, and it may be possible to put the post at any location by design, rather than working around the table. This may allow a shorter boom to reach the area of use, allowing less force to move it, and less bulky construction of the boom and base. Likewise, it may be possible to situate the support closer than a ceiling mounted system where ceiling obstacles may necessitate longer booms. It also obviates the need for ceiling tracks since the post may be moved by moving the table. Many variations of this system are possible including different shapes of the frame or table, numbers of floor contacts or wheels, function of column including any of the various mechanisms described elsewhere such as ceiling or floor docking, conventional boom with conventional trolley and balancer arrangement directly below trolley, absence of motorized drive, use of any other type of arm mechanism including robot arms, holonomic arms, or articulating arm systems of all types, or arms extending horizontally from the table/stand and attaching in a non-overhead manner as described in FIG. 11, or any of numerous mechanisms of counterbalancing the radiation protection system.

The telescoping boom has the advantage of permitting the end of the boom to be retracted when overhead obstacles are encountered, such as the image intensifier, as seen in the Figure. With the telescoping boom design in FIG. 20, the operator is directly underneath the end of the boom, so the boom end will not collide with objects that are not directly overhead of the operator. There are many possible modifications and variations of the mobile floor stand system and/or the manipulator-type arm discussed thus far. However, the following example embodiments are not to be construed as limiting the scope of disclosure or claims herein with regard to the scope and spirit of the present invention.

If desired another stabilization and safety mechanism can be built-in to the portable floor-based suspension system: the base, stand, or table can attach to the floor via a component that slips down into a mechanism in the floor that grips it. This could be a hole in the floor with internal teeth or some other mechanical binding system to grip a table component—such as a rod or key—that inserts into it. A plurality of these mechanisms could be employed. The action of locking the table to the floor can be the required mechanism for unlocking another lock on the tabletop, which allows the articulating/manipulator/balancing arm to swing out from its docked position over the table. The arm would then be available for suspending the radiation shield/garment for operations. After use, the shield/garment/apron-suspending arm could then be swung back over the table top so that the table, arm, and garment are stable without the floor lock. When docked over the table, a lock can automatically activate to keep all components in position. If desired, the docking and locking action can also simultaneously deactivate the locking/binding mechanism in the floor so that it is unlocked, thus releasing the table from the floor and allowing it to be moved.

As discussed above, FIGS. 10-20 depict a variety of suspended radiation protection devices wherein a significant portion of the weight of the apparatus is supported by the floor, although it is contemplated that many alternative embodiments are possible within the scope of this invention. It is noted that alternative embodiments may include various components disclosed herein. For example, any of the different overhead or non-overhead suspension systems disclosed herein may be used on any device. Jib arms may be used where articulating arms are described, and vice versa. Motorized components may facilitate movement of the tables or stands, or movement of the suspension components such as the trolley. Other devices commonly known in the art besides wheels may be used to facilitate table motion, such as belts. A track may be present in the floor that supports and guides the table, which may ride on the tracks on wheels, rollers, or other common mechanisms. The tables or stands may be stabilized by secure, detachable attachment of one or more legs or components to the floor in fixed locations, wherein the tables or stands may not be slid or rolled about the floor once attached. This could also stabilize the table from tipping due to the cantilevered load.

In various contemplated embodiments, stability may be provided by detachable or non-detachable connections to the tracks upon which the devices ride, slide or roll. Wheels, rollers or bearings positioned on the legs, or the bottoms of the stands or tables, may be capable of sliding or rolling inside a track which is attached to the floor, or imbedded within this fixed surface. This track could be securably attached to the floor so that the table or stand, once engaged in the track, could not be pulled away from the floor without substantive force, and therefore would not tip or fall. This engagement could be permanent, or semi-permanent and accomplished using mechanisms widely known in the art. A safety mechanism such as a mechanical lock or detent could be employed to prevent accidental dislodgement and de-stabilization of the device. Likewise, a single track or multiple tracks could be used for stabilizing the system disclosed herein. In the event of a single track, it could be attachable to the legs or side of the table opposite the suspended load, to prevent that side from rising up.

Stabilization could also be provided through different means. A counterweight may be present in a remote location from the remainder of stand, base, table, or suspended apparatus. For example, it could be attached to a rigid arm extending in the opposite direction relative to the suspended device, thus counterbalancing it. It could be positioned above head level to remain free of personnel motion. It could be positioned lower to be free of obstructions higher in the room. The combination of weight and arm length could be chosen to provide the necessary counterbalancing effect while addressing other logistical considerations of each application or operating suite. The counterweight arm could be stationary, or it could be movable to allow optimization of its position. It could be linked with the arm for the suspended radiation protection device to remain in ideal counterbalancing position during use of the system.

While the invention has been particularly shown and described with reference to a various embodiments, it will be understood by those skilled in the art that various changes in form and detail may be made therein without departing from the spirit and scope of the invention.

I claim:

1. A protection apparatus, comprising:
a garment that substantially contours to an operator's body wherein the garment is operable to protect the operator from a substantial portion of radiation;
a frame that substantially contours to the operator's body wherein the frame is operable to support the garment separate from the operator and is operable to substantially maintain its substantially contoured shape in the absence of the operator; and,
a suspension assembly operable to support the weight of the frame and garment relative to the operator wherein the suspension assembly includes at least one rotatable arm.

2. A protection apparatus, comprising:
a garment that substantially contours to an operator's body wherein the garment is operable to protect the operator from a substantial portion of radiation;
a frame that substantially contours to the operator's body wherein the frame is operable to support the garment separate from the operator and is operable to substantially maintain its substantially contoured shape in the absence of the operator;
a suspension assembly operable to support the weight of the frame and garment relative to the operator; and,
at least one holonomic manipulator arm.

3. A protection apparatus, comprising:
a garment that substantially contours to an operator's body wherein the garment is operable to protect the operator from a substantial portion of radiation;
a frame that substantially contours to the operator's body wherein the frame is operable to support the garment separate from the operator and is operable to substantially maintain its substantially contoured shape in the absence of the operator; and,
a suspension assembly operable to support the weight of the frame and garment relative to the operator wherein the frame and suspension assembly are secured together with at least one rotatable pitch axle connection.

4. A protection apparatus, comprising:
a garment that substantially contours to an operator's body wherein the garment is operable to protect the operator from a substantial portion of radiation;
a frame that substantially contours to the operator's body wherein the frame is operable to support the garment separate from the operator and is operable to substantially maintain its substantially contoured shape in the absence of the operator;

a suspension assembly operable to support the weight of the frame and garment relative to the operator wherein the suspension assembly includes a mobile floor stand wherein the floor stand includes means for docking the mobile floor stand to a floor surface.

5. A protection apparatus, comprising:

a garment that substantially contours to an operator's body wherein the garment is operable to protect the operator from a substantial portion of radiation;

a frame that substantially contours to the operator's body wherein the frame is operable to support the garment separate from the operator and is operable to substantially maintain its substantially contoured shape in the absence of the operator; and, a suspension assembly operable to support the weight of the frame and garment relative to the operator wherein the suspension assembly includes a mobile floor stand wherein the mobile floor stand is integrated with a back table.

6. A protection apparatus, comprising:

a garment that substantially contours to an operator's body wherein the garment is operable to protect the operator from a substantial portion of radiation;

a frame that substantially contours to the operator's body wherein the frame is operable to support the garment separate from the operator and is operable to substantially maintain its substantially contoured shape in the absence of the operator; and, a suspension assembly operable to support the weight of the frame and garment relative to the operator wherein the suspension assembly includes a mobile floor stand; and, a jib-boom system.

7. A protection apparatus, comprising:

a garment that substantially contours to an operator's body wherein the garment is operable to protect the operator from a substantial portion of radiation;

a frame that substantially contours to the operator's body wherein the frame is operable to support the garment separate from the operator and is operable to substantially maintain its substantially contoured shape in the absence of the operator;

a suspension assembly operable to support the weight of the frame and garment relative to the operator;

a portable track stand or table upon which the suspension assembly is attached; and, a floor hook for stabilizing the portable track stand or table.

8. A method, comprising:

suspending with a suspension assembly a radiation protection system which includes a garment and a face shield secured to a frame operable to protect an operator from a substantial portion of radiation, wherein the radiation protection system includes a joint in substantial proximity of the center of gravity of the radiation protection system allowing motion in at least one degree of freedom, wherein the frame and suspension assembly are secured together with at least one rotatable pitch axle connection;

contouring a portion of the frame to the operator's body; and, engaging the operator with the protection system.

9. A method, comprising:

suspending with a suspension assembly a radiation protection system which includes a garment and a face shield secured to a frame operable to protect an operator from a substantial portion of radiation wherein the suspension assembly is detachably connected to a mobile floor stand integrated with a medical operations back-table;

contouring a portion of the frame to the operator's body; and, engaging the operator with the protection system.

10. A method, comprising:

suspending with a suspension assembly a radiation protection system which includes a garment and a face shield secured to a frame operable to protect an operator from a substantial portion of radiation wherein the suspension assembly is detachably connected to a mobile floor stand wherein the mobile floor stand is detachably secured to a floor;

contouring a portion of the frame to the operator's body; and, engaging the operator with the protection system.

11. A method, comprising:

suspending with a suspension assembly a radiation protection system which includes a garment and a face shield secured to a frame operable to protect an operator from a substantial portion of radiation wherein the suspension assembly is detachably connected to a mobile floor stand wherein the mobile floor stand is detachably secured to a ceiling;

contouring a portion of the frame to the operator's body; and, engaging the operator with the protection system.

* * * * *